(12) United States Patent
Grzybowski et al.

(10) Patent No.: US 8,940,895 B2
(45) Date of Patent: Jan. 27, 2015

(54) HETEROCYCLIC FLUORESCENT DYES AND METHOD OF PRODUCTION THEREOF

(71) Applicant: BASF SE, Ludwigshafen (DE)

(72) Inventors: Marek Grzybowski, Szczecin (PL); Daniel T. Gryko, Warsaw (PL)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/363,104

(22) PCT Filed: Dec. 17, 2012

(86) PCT No.: PCT/EP2012/075762
§ 371 (c)(1),
(2) Date: Jun. 5, 2014

(87) PCT Pub. No.: WO2013/092474
PCT Pub. Date: Jun. 27, 2013

(65) Prior Publication Data
US 2014/0357869 A1    Dec. 4, 2014

(30) Foreign Application Priority Data
Dec. 21, 2011 (PL) .......................... P397479

(51) Int. Cl.
| | | |
|---|---|---|
| *C07D 471/22* | (2006.01) | |
| *H01L 51/00* | (2006.01) | |
| *C09B 57/00* | (2006.01) | |
| *H01L 51/42* | (2006.01) | |

(52) U.S. Cl.
CPC .......... *H01L 51/0072* (2013.01); *C09B 57/004* (2013.01); *H01L 51/0071* (2013.01); *H01L 51/4253* (2013.01)
USPC ................ 546/41; 313/504; 313/499; 546/31

(58) Field of Classification Search
USPC ............................. 546/41, 31; 313/499, 504
See application file for complete search history.

(56) References Cited

U.S. PATENT DOCUMENTS

| | | |
|---|---|---|
| 2003/0021913 A1 | 1/2003 | O'Neill et al. |
| 2006/0013549 A1 | 1/2006 | Shtein et al. |
| 2007/0079867 A1 | 4/2007 | Chittibabu et al. |
| 2011/0004004 A1 | 1/2011 | Hao et al. |

FOREIGN PATENT DOCUMENTS

| | | |
|---|---|---|
| WO | WO 03/052841 A1 | 6/2003 |
| WO | WO 2004/112161 A2 | 12/2004 |
| WO | WO 2007/113107 A1 | 10/2007 |
| WO | WO 2009/047104 A2 | 4/2009 |

OTHER PUBLICATIONS

International Search Report issued Apr. 23, 2013 in PCT/EP2012/075762.
Georg M. Fischer, et al., "Selective NIR chromophores: Bis(Pyrrolopyrrole) Cyanines" Angewandte Chemie International Edition, vol. 50, No. 6, XP55057949, Feb. 7, 2011, pp. 1406-1409.
Georg Michael Fischer, et al., "Asymmetric PPCys: Strongly fluorescing NIR labels" Chemical Communications, vol. 46, No. 29, XP55057947, Jan. 1, 2010, pp. 5289-5291.
Marek Grzybowski, et al., "Bright, Color-Tunable Fluorescent Dyes Based on π-Expanded Diketopyrrolopyrroles" Organic Letters, vol. 14, No. 11, XP55057863, Jun. 1, 2012, pp. 2670-2673.

*Primary Examiner* — Charanjit Aulakh
(74) *Attorney, Agent, or Firm* — Oblon, Spivak, McClelland, Maier & Neustadt, L.L.P.

(57) ABSTRACT

The invention relates to novel compounds of formula (III) that can be used as heterocyclic dyes of unique structure and properties. These dyes can be obtained in a three-step synthesis from simple substrates.

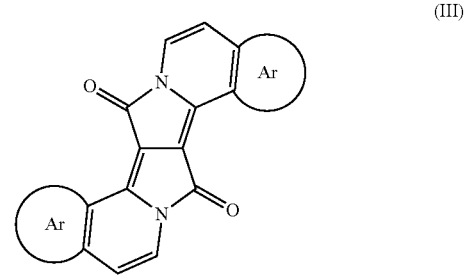

(III)

18 Claims, No Drawings

HETEROCYCLIC FLUORESCENT DYES AND METHOD OF PRODUCTION THEREOF

The invention relates to novel compounds that can be used as heterocyclic dyes of unique structure and properties. These compounds can be obtained in a three-step synthesis from simple substrates.

Organic dyes are known, which are diketopyrrolopyrroles (DPPs) of formula (I), which are employed as pigments, used in the production of durable paints and varnishes.

There is still a need for stable water-insoluble organic pigments, which might find application in the dyeing industry. In addition, the development of fluorometric techniques and the extensive use thereof in modern biomedical techniques and diagnostics (e.g. optical imaging) means there is steady growth in demand for new compounds with improved fluorescence properties in the visible range. Provision of compounds with high fluorescence quantum yield is required.

The above problems were solved unexpectedly in the present invention.

The invention relates to novel compounds of formula (III):

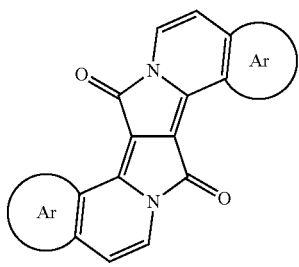

(III)

where Ar denotes a homo- or heteroaromatic system.

The homo- or heteroaromatic system (Ar) is selected from the group consisting of benzene, furan, thiopene, pyrrole, selenophene, benzofuran, benzothiophene, indole, benzoselenophene, thieno[2,3-b]thiophene and thieno[3,2-b]thiophene.

The homo- or heteroaromatic system may be unsubstituted, or substituted.

Examples of substituents are halogen, especially F; cyano, $C_1$-$C_{25}$alkoxy, $C_1$-$C_{25}$alkyl, $C_1$-$C_{25}$alkyl substituted with one or more halogen atoms, especially F;

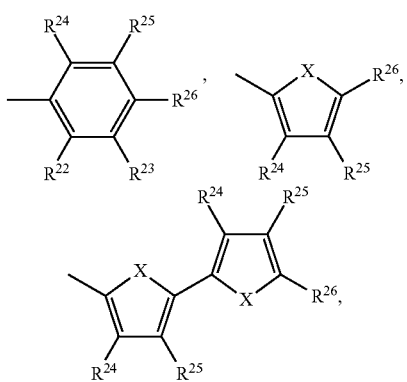

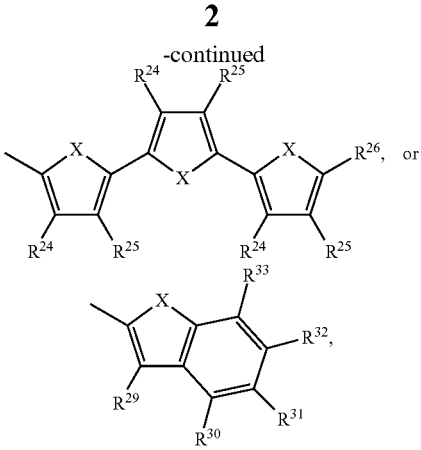

wherein $R^{22}$ to $R^{26}$ and $R^{29}$ to $R^{33}$ are as defined below.

Specific examples of homo- or heteroaromatic system (Ar) are shown below:

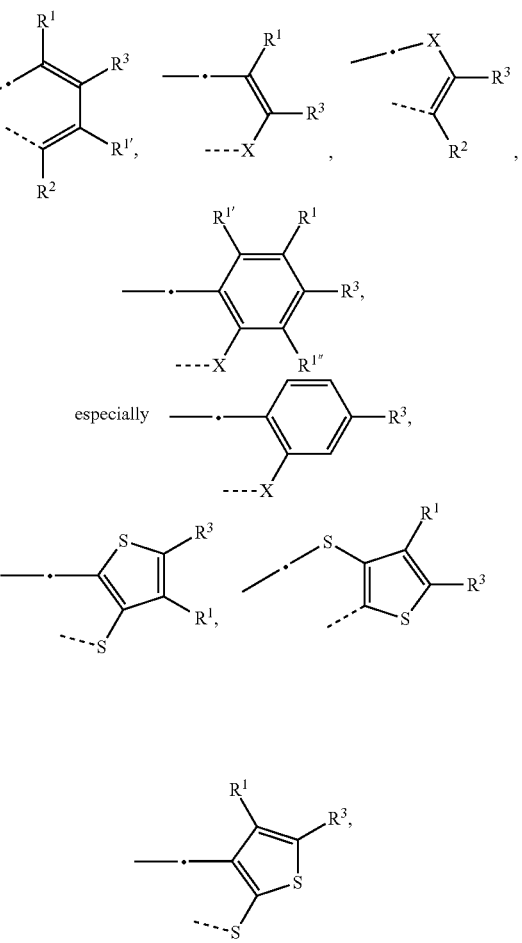

wherein the dotted lines denotes the bonds to the 6-membered ring (the dotted line —·— indicates the bond to the carbon atom in para-position to the nitrogen atom, the dotted line ----- indicates the bond to the carbon atom in meta-position to the nitrogen atom)

$R^1$, $R^{1'}$ and $R^{1'''}$ are independently of each other H, halogen, especially F, cyano, $C_1$-$C_{25}$alkoxy, $C_1$-$C_{25}$alkyl substituted with one or more halogen atoms, or $C_1$-$C_{25}$alkyl, $R^2$ is H, halogen, especially F, cyano, $C_1$-$C_{25}$alkoxy, or $C_1$-$C_{25}$alkyl, $R^3$ is halogen, especially F, Cl, or I, very especially F; cyano, $C_1$-$C_{25}$alkoxy, $C_1$-$C_{25}$alkyl substituted with one or more halogen atoms, $C_1$-$C_{25}$alkyl,

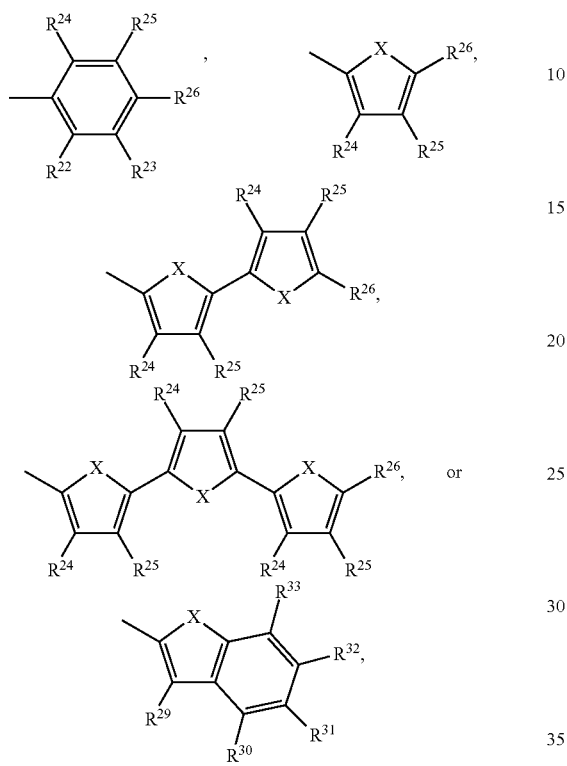

wherein $R^{22}$ to $R^{25}$ and $R^{29}$ to $R^{33}$ represent independently of each other H, halogen, cyano, $C_1$-$C_{25}$alkoxy, $C_1$-$C_{25}$alkyl substituted with one or more halogen atoms, especially F, or $C_1$-$C_{25}$alkyl, and $R^{26}$ is H, halogen, especially F, cyano, phenyl, $C_1$-$C_{25}$alkoxy, $C_1$-$C_{25}$alkyl substituted with one or more halogen atoms, or $C_1$-$C_{25}$alkyl;

X is O, S, Se, or $NR^4$, $R^4$ is hydrogen, $C_6$-$C_{18}$aryl; $C_6$-$C_{18}$aryl which is substituted by $C_1$-$C_{18}$alkyl, or $C_1$-$C_{18}$alkoxy; $C_1$-$C_{25}$alkyl, which may optionally be interrupted by one or more oxygen or sulphur atoms and/or is optionally substituted by one or more halogen atoms, especially F; or $C_7$-$C_{25}$arylalkyl.

In a preferred embodiment of the present invention the compound according to the invention is characterized in that the homo- or heteroaromatic system is selected from the group consisting of unsubstituted benzene, benzene derivatives containing one or more alkoxy groups in ortho, meta and para positions, derivatives of thiophene, benzofuran, indole, benzothiophene.

In another preferred embodiment of the present invention the compound according to the invention is characterized in that the homo- or heteroaromatic system is selected from the group consisting of unsubstituted benzene, benzene derivatives containing one or more alkoxy groups in ortho, meta and para positions, derivatives of benzofuran, indole, benzothiophene.

Preferably the compound according to the invention is selected from the group consisting of the following compounds of formulae:

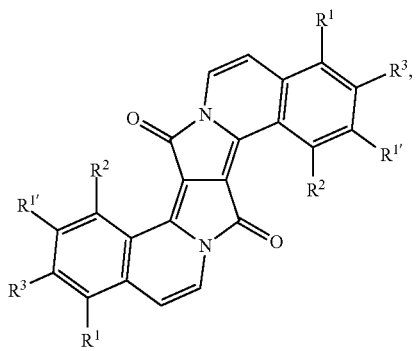
(IIIa)

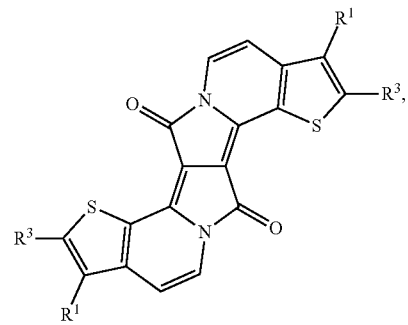
(IIIb)

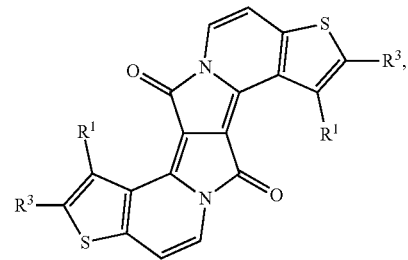
(IIIc)

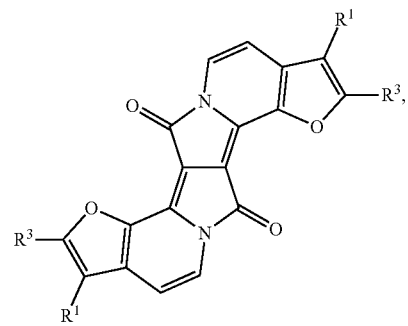
(IIId)

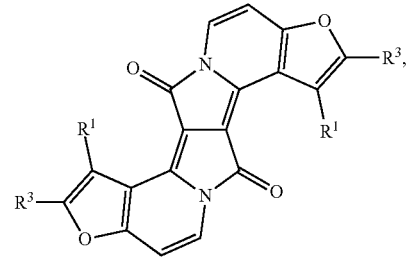
(IIIe)

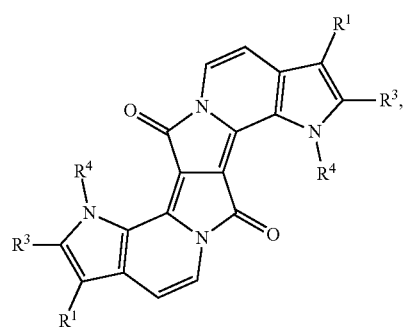
(IIIf)

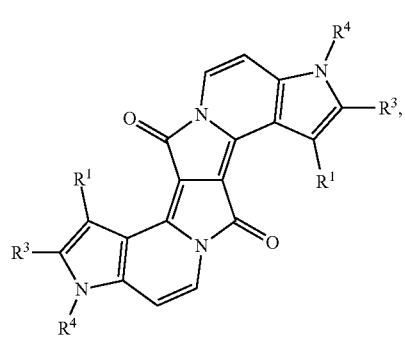
(IIIg)

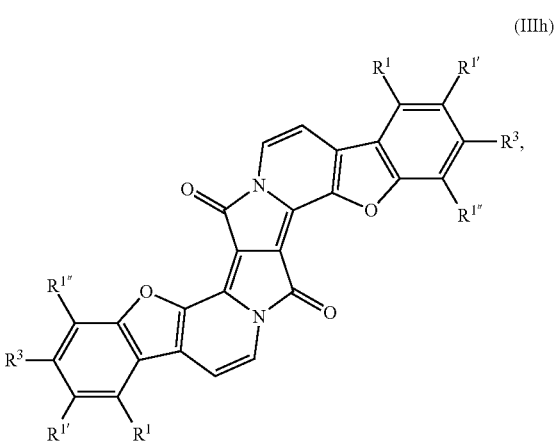
(IIIh)

(IIIi)

(IIIj)

(IIIk)

(IIIl)

and
wherein $R^1$, $R^{1'}$, $R^{1''}$, $R^2$, $R^3$ and $R^4$ are as defined above.
Compounds of formula (IIIa), (IIIb), (IIId), (IIIf), (IIIh), (IIIi) and (IIIj) are preferred. Compounds of formula (IIIb), (IIId) and (IIIj) are most preferred.

More preferably the compound according to the invention is selected from the group consisting of the following compounds of formulae:

(IIIa′)

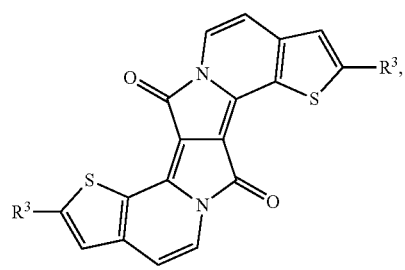 (IIIb′)
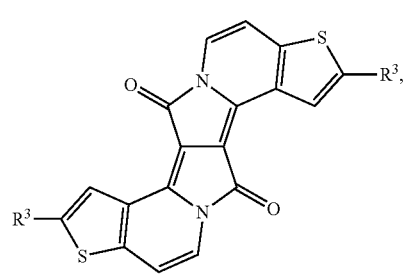 (IIIc′)
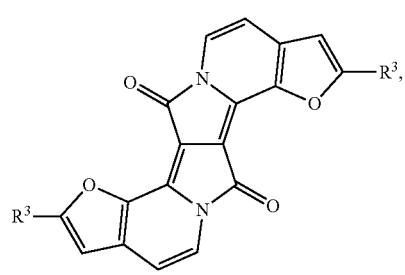 (IIId′)
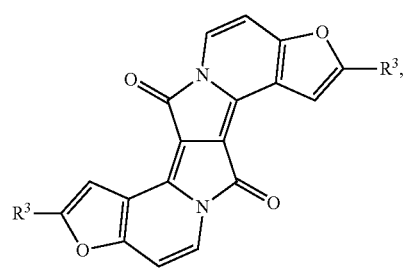 (IIIe′)
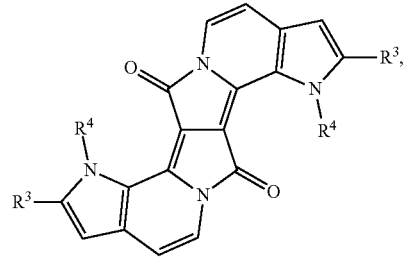 (IIIf′)
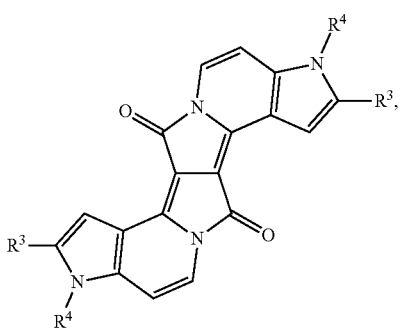 (IIIg′)
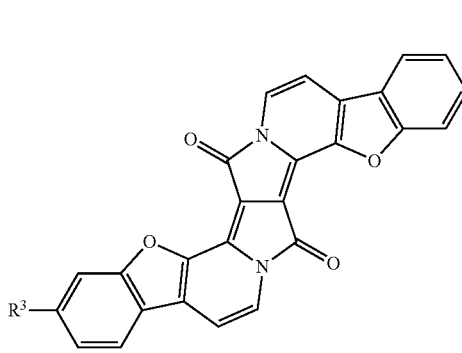 (IIIh′)
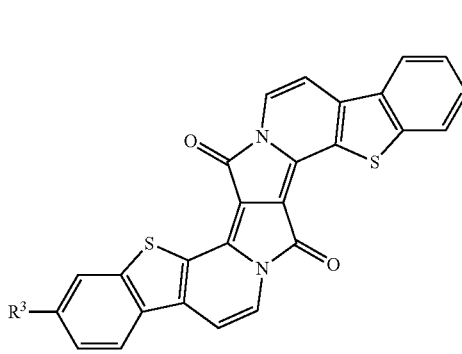 (IIIi′)
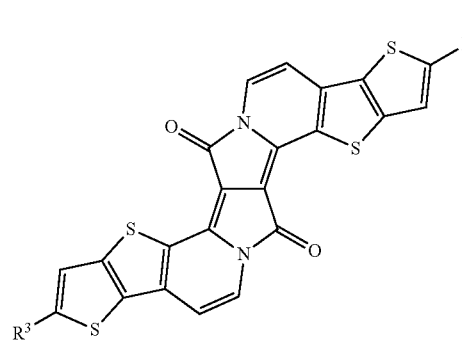 (IIIj′)
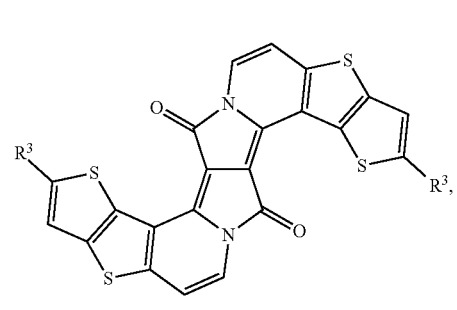 (IIIk′) and

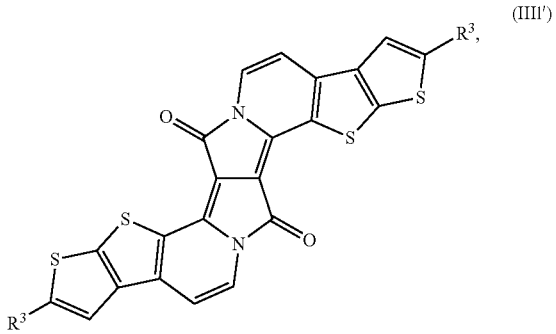
(IIII')

wherein $R^1$, $R^{1'}$, $R^3$ and $R^4$ are as defined above. Compounds of formula (IIIa'), (IIIb'), (IIId'), (IIIf'), (IIIh'), (IIIi') and (IIIj') are preferred. Compounds of formula (IIIb'), (IIId') and (IIIj') are most preferred.

Preferably, $R^1$, $R^{1'}$ and $R^{1'''}$ are independently of each other H, $C_1$-$C_{25}$alkoxy, or $C_1$-$C_{25}$alkyl. More preferred, $R^1$, $R^{1'}$ and $R^{1'''}$ are independently of each other hydrogen, or $C_1$-$C_{25}$alkyl, most preferred hydrogen.

Preferably, $R^2$ is H, $C_1$-$C_{25}$alkoxy, or $C_1$-$C_{25}$alkyl. More preferred, $R^2$ is hydrogen, or $C_1$-$C_{25}$alkyl. Most preferred $R^2$ is hydrogen.

Preferably, $R^3$ is F, trifluoromethyl, cyano, $C_1$-$C_{25}$alkyl, a group of formula

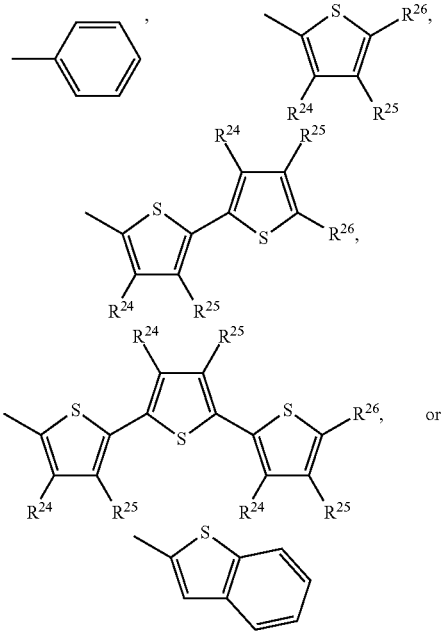

wherein $R^{24}$ to $R^{26}$ are as defined above and are preferably H, or $C_1$-$C_{25}$alkyl, more preferably H. More preferred, $R^3$ is F, cyano, $C_1$-$C_{25}$alkyl,

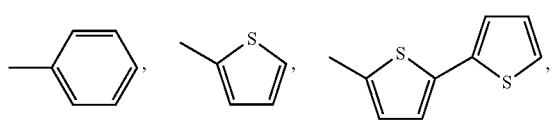

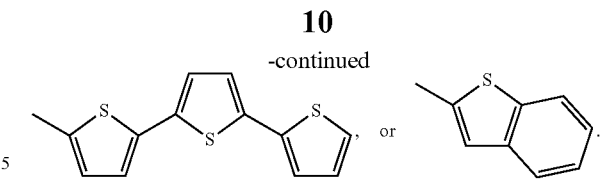
or

Most preferred, $R^3$ is cyano,

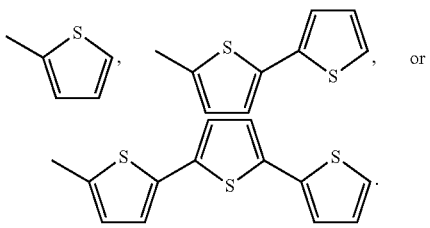

Preferably, $R^4$ is hydrogen, or $C_1$-$C_{25}$alkyl, which may optionally be interrupted by one or more oxygen or sulphur atoms. More preferably, $R^4$ is $C_1$-$C_{25}$alkyl.

Preferably, X is O, S, or Se, more preferably X is O, or S, most preferred, X is S.

In a preferred embodiment the present invention is directed to compounds of formula (IIIa), (IIIb), (IIIc), (IIId), (IIIe), (IIIf), (IIIg), (IIIh), (IIIi), (IIIj), (IIIk), and (IIIl), especially (IIIa), (IIIb), (IIId), (IIIf), (IIIh), (IIIi) and (IIIj), very especially (IIIb), (IIId) and (IIIj); wherein $R^1$, $R^{1'}$ and $R^{1'''}$ are independently of each other H, $C_1$-$C_{25}$alkoxy, or $C_1$-$C_{25}$alkyl, $R^2$ is H, $C_1$-$C_{25}$alkoxy, or $C_1$-$C_{25}$alkyl, $R^3$ is F, trifluoromethyl, cyano, $C_1$-$C_{25}$alkyl, a group of formula

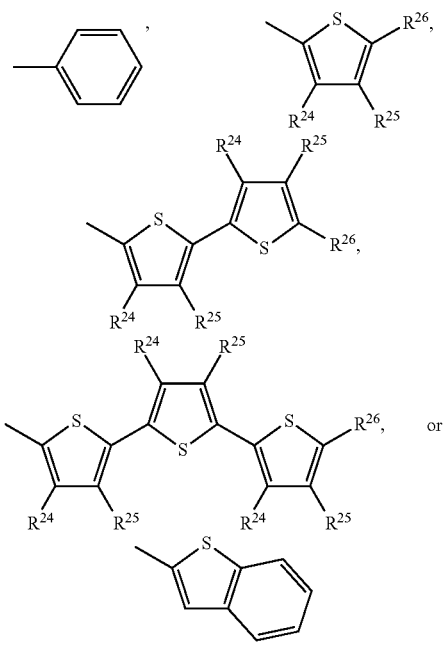

wherein $R^{24}$ to $R^{26}$ are as defined above, $R^4$ is hydrogen, or $C_1$-$C_{25}$alkyl, which may optionally be interrupted by one or more oxygen or sulphur atoms, and X is O, S, or Se. $R^{24}$ to $R^{26}$ are preferably H, or $C_1$-$C_{25}$alkyl, In a more preferred embodiment the present invention is directed to compounds of formula (IIIa), (IIIb), (IIIc), (IIId), (IIIe), (IIIf), (IIIg), (IIIh), (IIIi), (IIIj), (IIIk), and (IIIl), especially (IIIa), (IIIb), (IIId), (IIIf), (IIIh), (IIIi) and (IIIj), very especially (IIIb), (IIId) and (IIIj); $R^1$, $R^{1''}$ and $R^{1''}$ are independently of each other hydrogen, or $C_1$-$C_{25}$alkyl, especially hydrogen; $R^2$ is hydrogen, or $C_1$-$C_{25}$alkyl, especially hydrogen, $R^3$ is F, cyano, $C_1$-$C_{25}$alkyl,

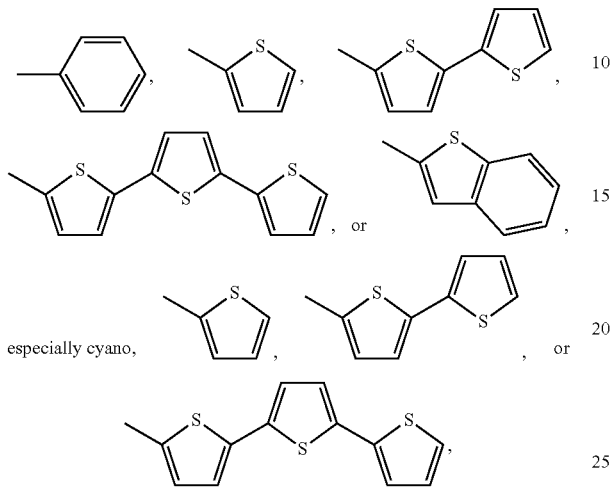

especially cyano,

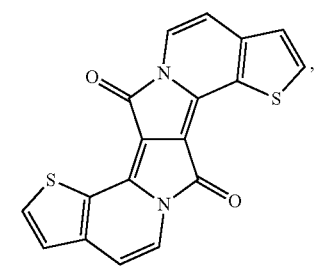

$R^4$ is $C_1$-$C_{25}$alkyl; and X is O, or S, especially S.

Preferably the compound according to the invention is selected from the group consisting of the following compounds of formulae 3a, 3b, 3c, 3d, 3e, 3f and 3g:

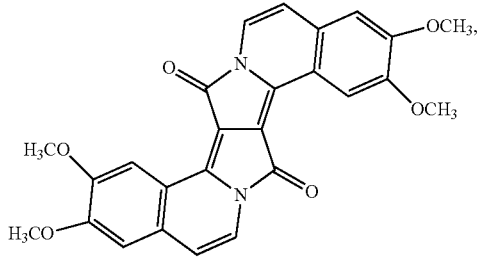

(3a)

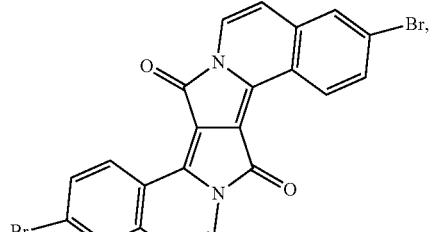

(3b)

(3c)

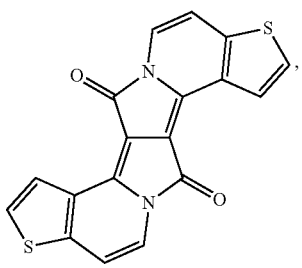

(3d)

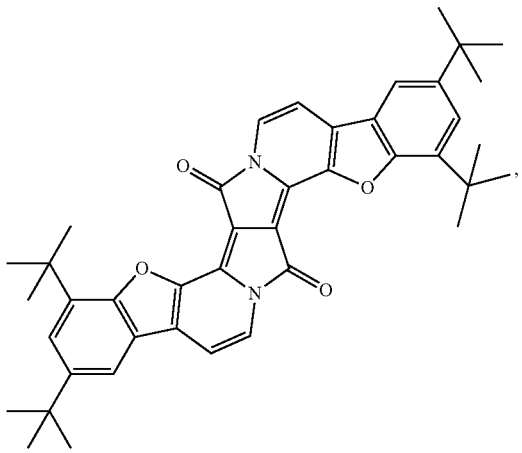

(3e)

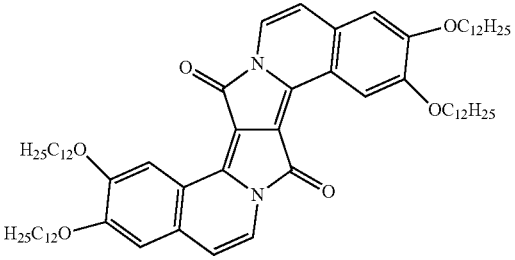

(3f)

and

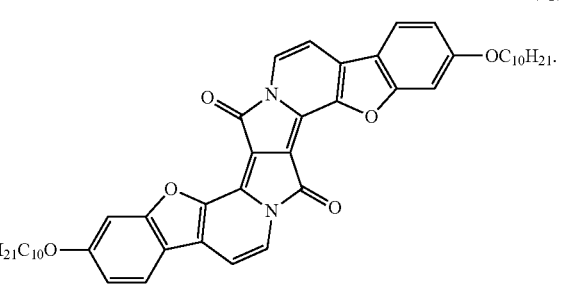

(3g)

In another preferred embodiment the compound according to the invention is selected from the group consisting of the following compounds of formulae 4a, 4b, and 4c:

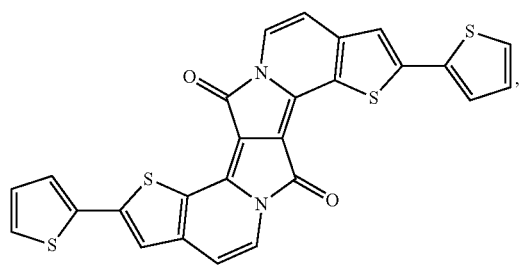
(4a)
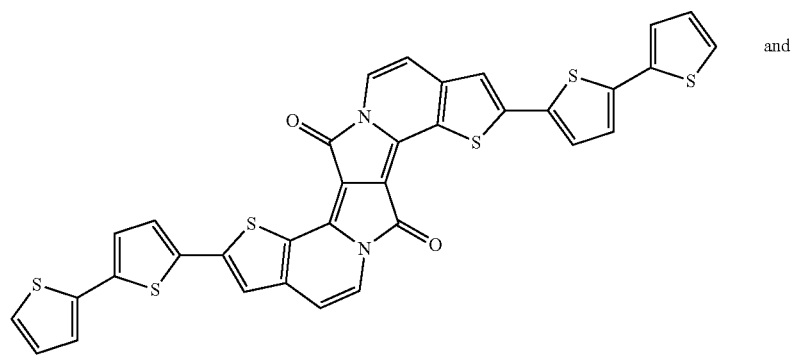
(4b)
and
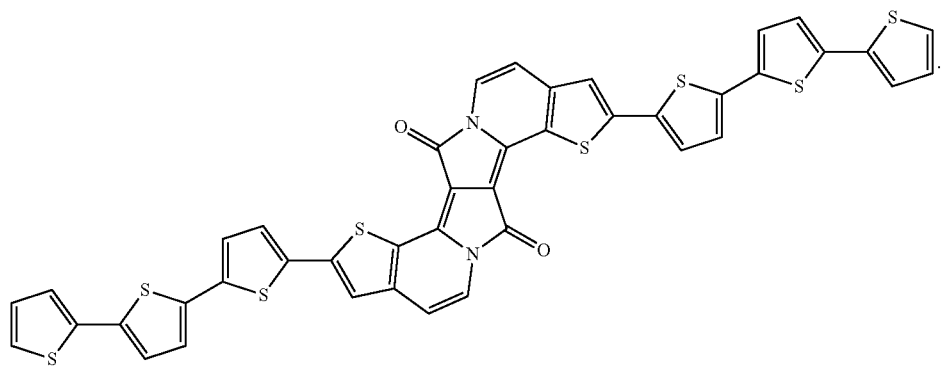
(4c)
Compound (4a) can, for example, be prepared starting from the DPP derivative (2c) optionally via the intermediate (5b) as shown in the reaction scheme below:
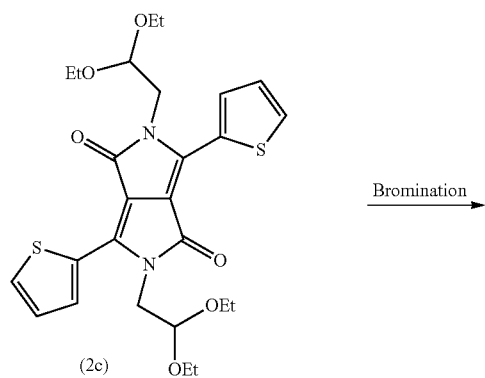
Bromination →

-continued

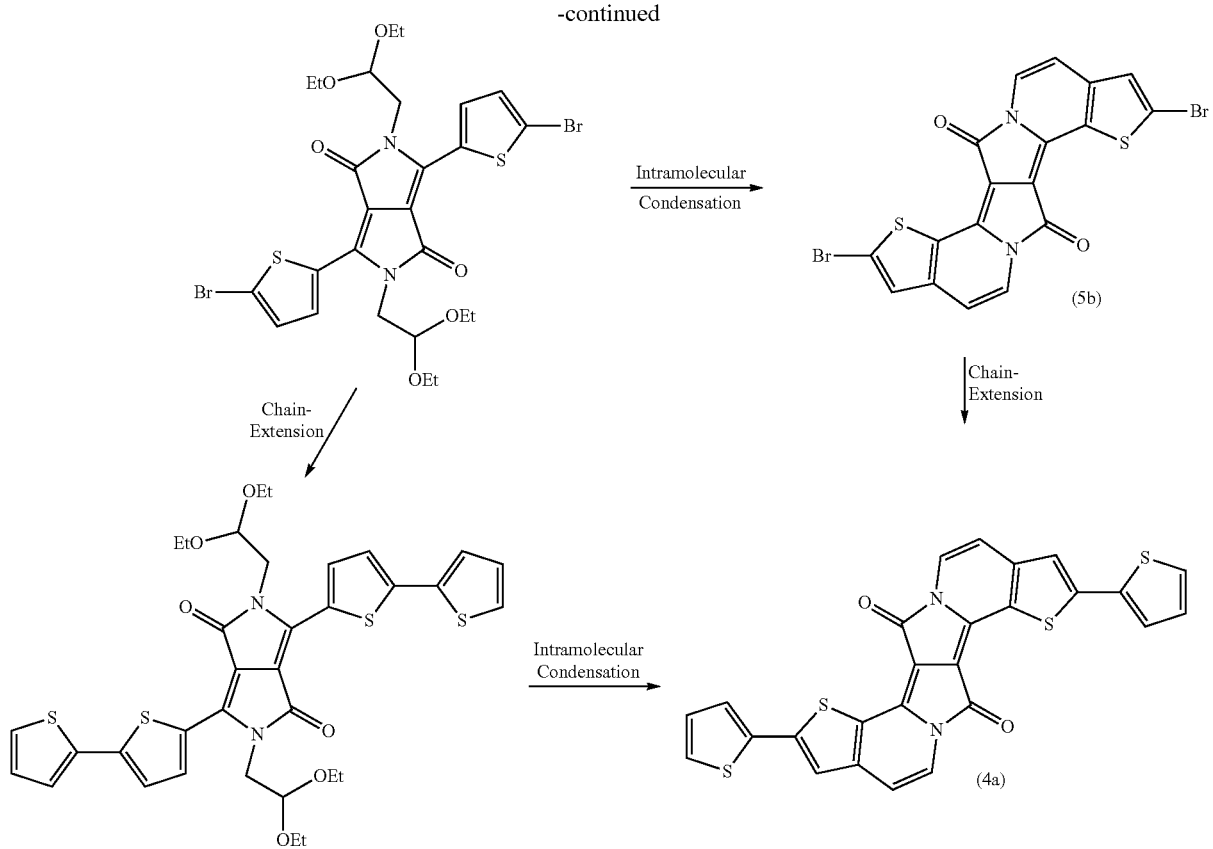

The bromination is carried out in a suitable solvent, like chloroform, using two equivalents of N-bromo-succinimide at a temperature between −30° C. and +50° C., preferably between −10° C. and room temperature, e.g. at 0° C.

The "chain-extension" of compound (5b), or the bromination product of DPP derivative (2c) with an additional thienyl residue can be effected, for example, by reaction with a mixture of 2-thienylboronic acid pinacol ester, $Pd_2(dba)_3$ [tris(dibenzylideneacetone)-dipalladium)] and tri-tert-butyl-phosphonium-tetrafluoroborate in tetrahydrofurane including a suitable base, such as, for example, $K_2CO_3$, $K_3PO_4$ and LiOH. The bromination and chain-extension of DPP derivatives is described in more detail on pages 17 to 19 of WO2009/047104. Compounds (4b) and (4c) can be prepared in analogous manner. WO2009/047104 discloses also possible starting DPP compounds for the synthesis of the compounds of formula (II).

Compounds of formula

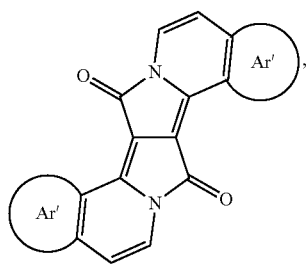
(V)

wherein Ar' is a homo- or heteroaromatic system, which is substituted by Cl, Br, or I, are intermediates in the production of other small molecules, or polymers, especially polymers which can be used as functional dyes in dye sensitized and bulk heterojunction solar cells, organic light emitting diodes, photodiodes, organic field effect transistors, fluorescence imaging, sensors and solid-state dye lasers.

Accordingly, the present invention is directed to compounds of formula

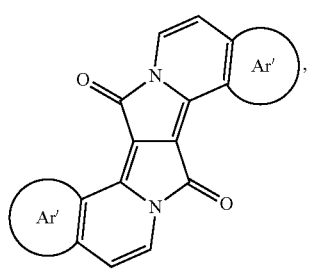
(V)

wherein Ar' denotes a homo- or heteroaromatic system, which is selected from

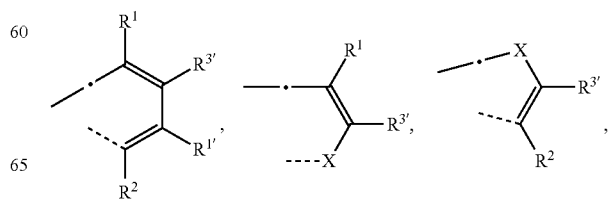

-continued

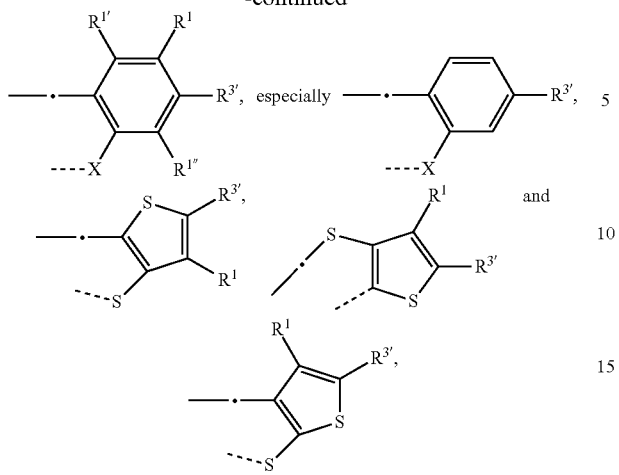

wherein the dotted lines denotes the bonds to the 6-membered ring (the dotted line ▬ ▪ ▬ indicates the bond to the carbon atom in para-position to the nitrogen atom, the dotted line ▬ ▬ ▬ ▬ ▬ indicates the bond to the carbon atom in meta-position to the nitrogen atom), wherein $R^1$, $R^{1'}$ and $R^{1'''}$ are independently of each other H, halogen, cyano, $C_1$-$C_{25}$alkoxy, $C_1$-$C_{25}$alkyl substituted with one or more halogen atoms, or $C_1$-$C_{25}$alkyl, $R^2$ is H, halogen, cyano, $C_1$-$C_{25}$alkoxy, or $C_1$-$C_{25}$alkyl, $R^{3'}$ is Cl, Br, or I,

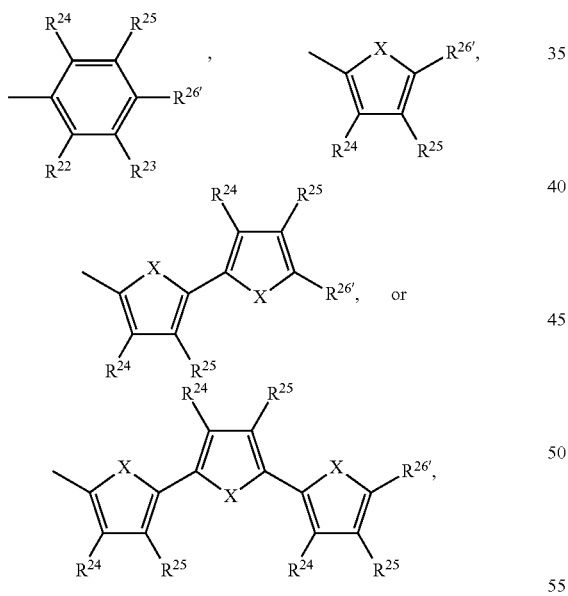

wherein $R^{22}$ to $R^{25}$ represent independently of each other H, halogen, cyano, $C_1$-$C_{25}$alkoxy, $C_1$-$C_{25}$alkyl substituted with one or more halogen atoms, or $C_1$-$C_{25}$alkyl, and $R^{26'}$ is Cl, Br, or I;

X is O, S, Se, or $NR^4$, $R^4$ is hydrogen, $C_6$-$C_{18}$aryl; $C_6$-$C_{18}$ aryl which is substituted by $C_1$-$C_{18}$alkyl, or $C_1$-$C_{18}$alkoxy; $C_1$-$C_{25}$alkyl, which may optionally be interrupted by one or more oxygen or sulphur atoms and/or is optionally substituted by one or more halogen atoms; or $C_7$-$C_{25}$arylalkyl.

In said embodiment compounds of formula

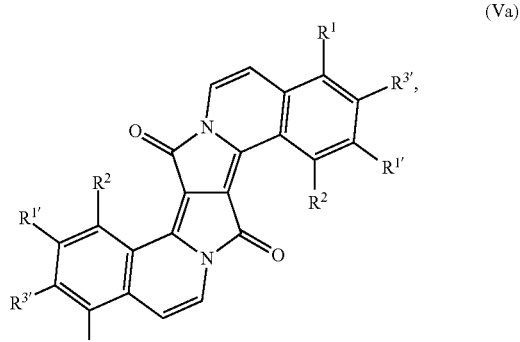
(Va)

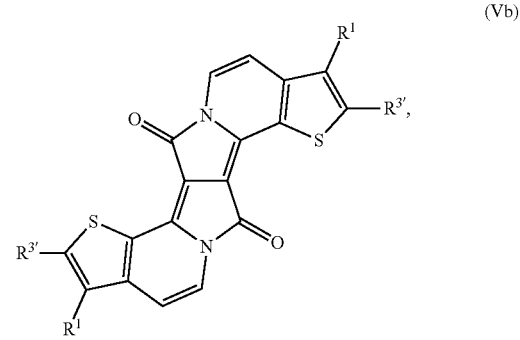
(Vb)

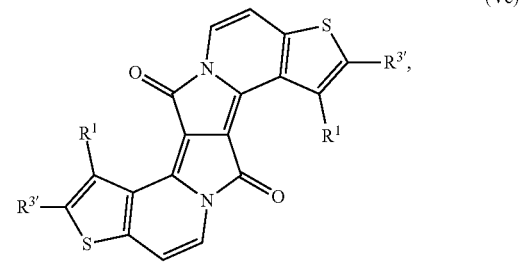
(Vc)

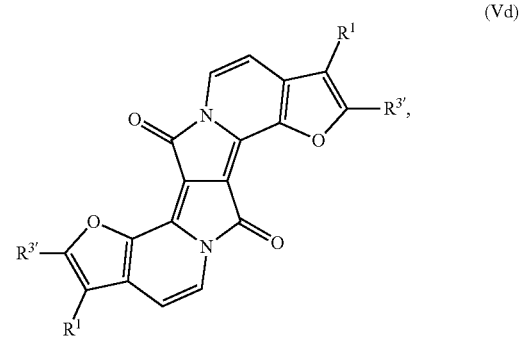
(Vd)

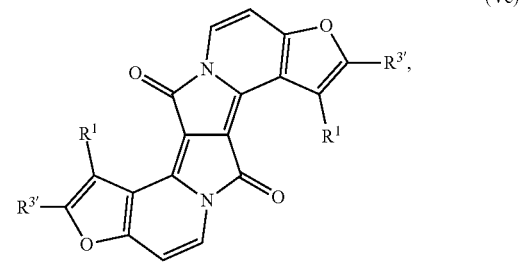
(Ve)

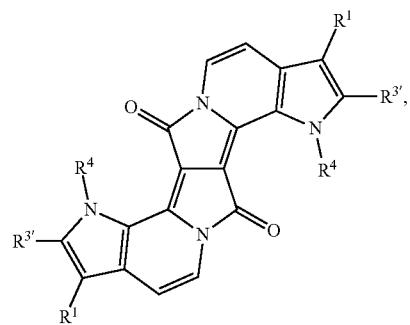
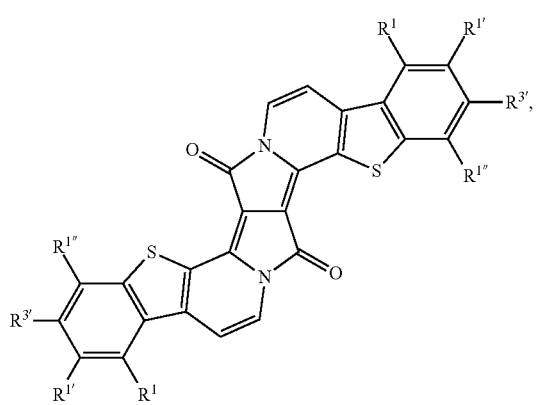
are preferred, wherein $R^1$, $R^{1'}$, $R^{1'''}$, $R^2$ and $R^4$ are as defined above and $R^{3'}$ is Cl, Br, or I. Compounds of formula (Va), (Vb), (Vd), (Vf), (Vh), (Vi) and (Vj) are preferred. Compounds of formula (Vb), (Vd) and (Vj) are most preferred.
In said embodiment compounds of formula -continued
(Vb')
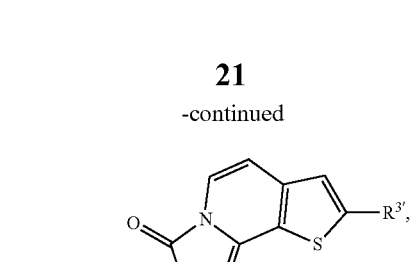
(Vc')
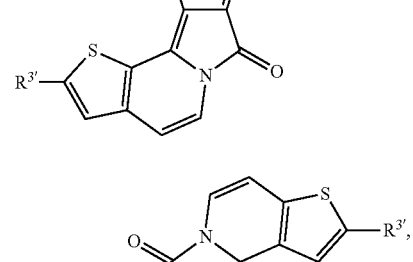
(Vd')
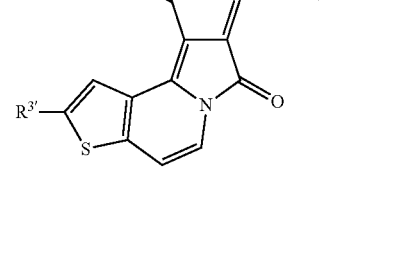
(Ve')
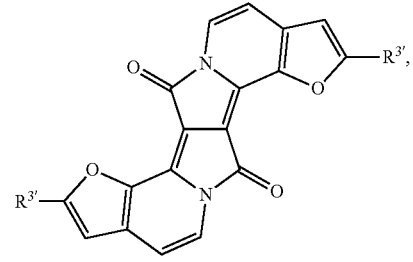
(Vf')
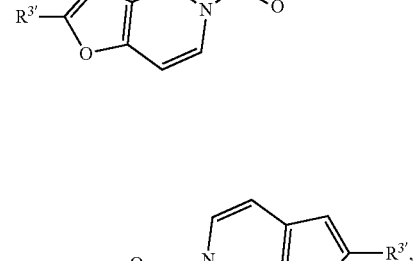
(Vg')
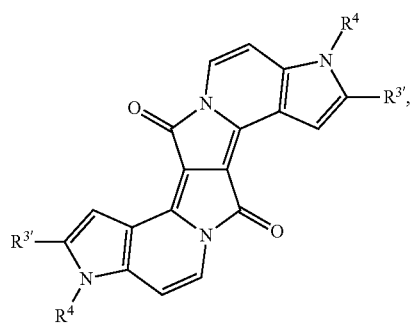
(Vh')
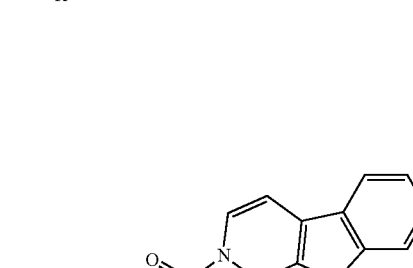
(Vi')
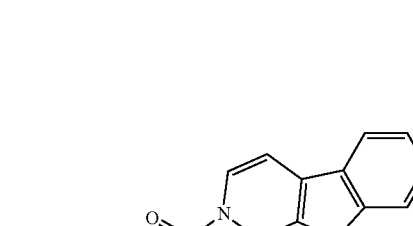
(Vj')
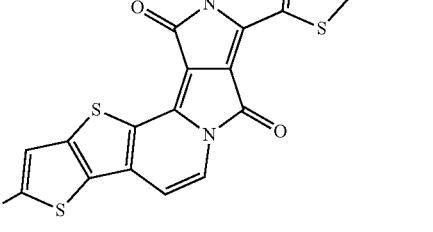

(Vk') 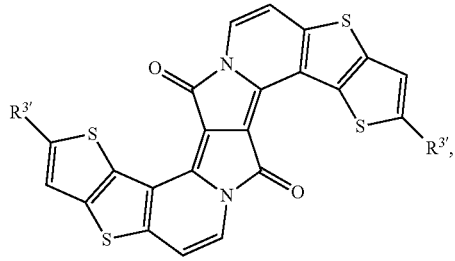
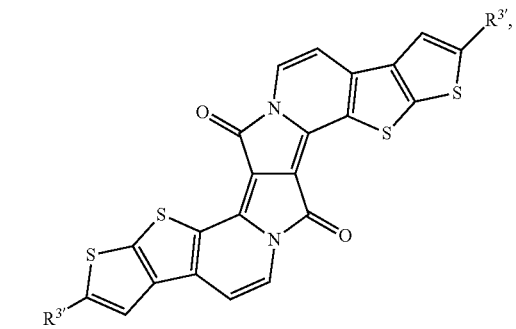 (Vl')
are more preferred, wherein $R^1$, $R^{1'}$ and $R^4$ are as defined above and $R^{3'}$ is Cl, Br, or I.
Compounds of formula (Va'), (Vb'), (Vd'), (Vf'), (Vh'), (Vi') and (Vj') are preferred. Compounds of formula (Vb'), (Vd') and (Vj') are most preferred.
For $R^1$, $R^{1'}$, $R^{1'''}$, $R^2$ and $R^4$ the same preferences apply as above.
Examples of such intermediates are shown below:
(3b) 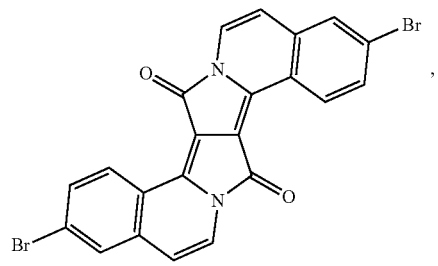
(5a) 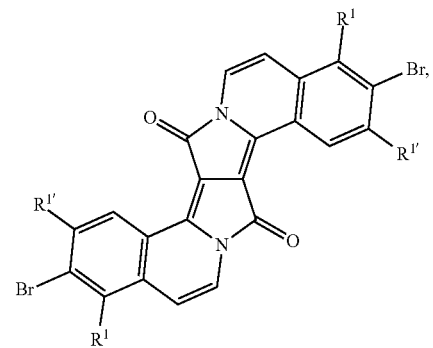
(5b) 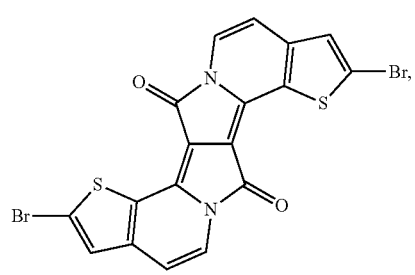
(5c) 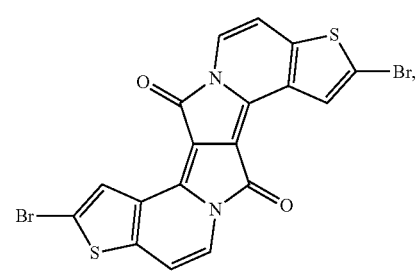
(5d) 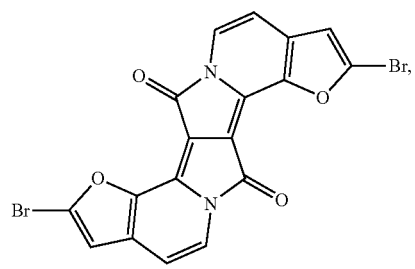
(5e) 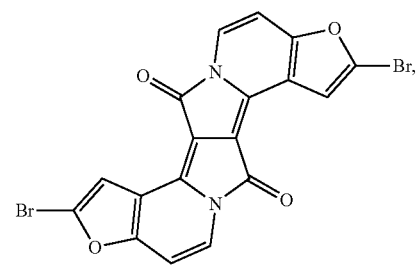

-continued
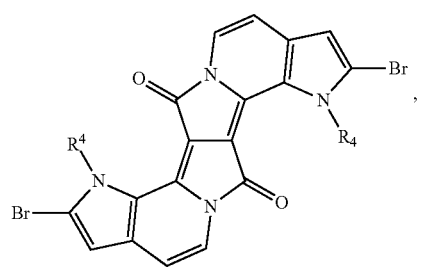
(5f)
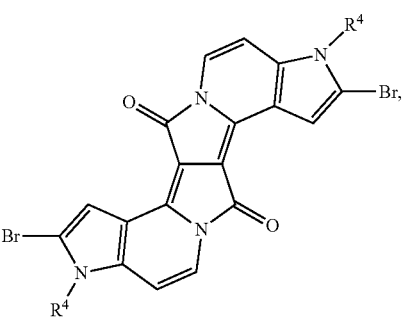
(5g)
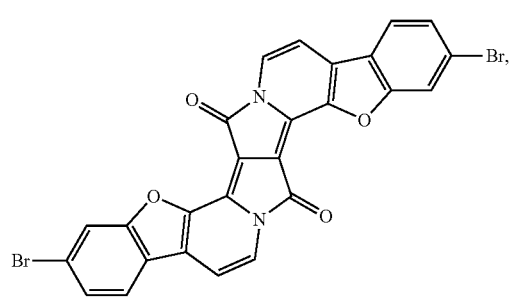
(5h)
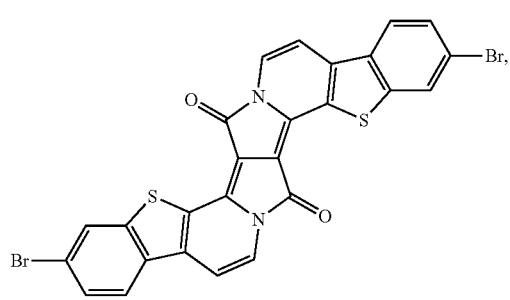
(5i)
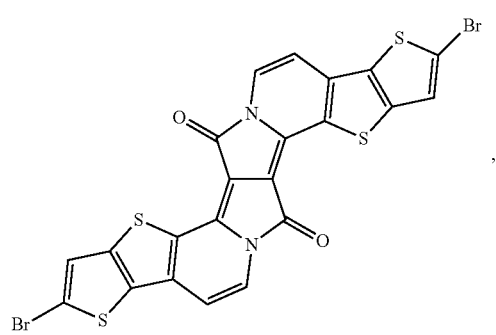
(5j)
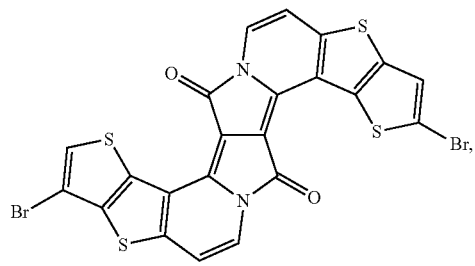
(5k)
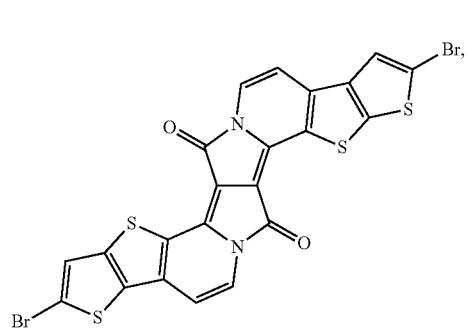
(5l)
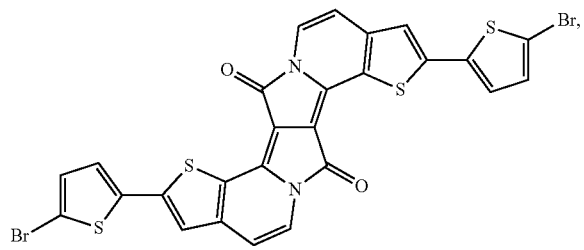
(5m)
and (5n)

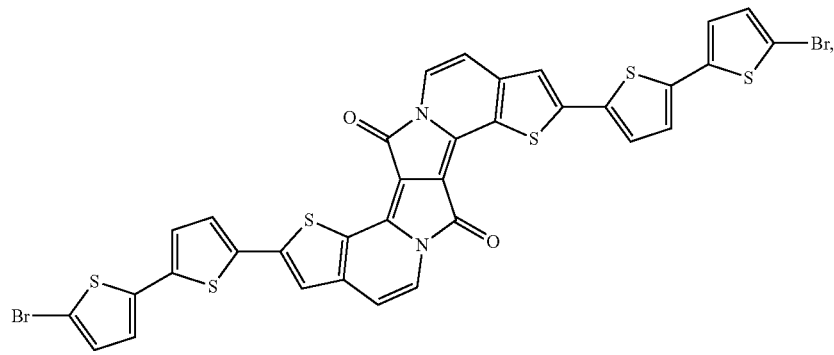

wherein $R^1$ and $R^{1'}$ are independently of each other hydrogen, or $C_1$-$C_{25}$alkyl, most preferred hydrogen. Compounds of formula (3b), (5b), (5d) and (5j) are preferred, compound (5b) is most preferred. Alternative embodiments of the present invention are shown below in form of claims 1 to 19:

1. A compound of formula (III):

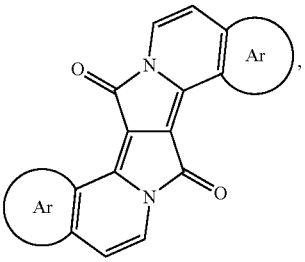

(III)

wherein Ar denotes a homo- or heteroaromatic system.

2. The compound of formula (III) according to claim 1, wherein Ar denotes a homo- or heteroaromatic system, which is selected from

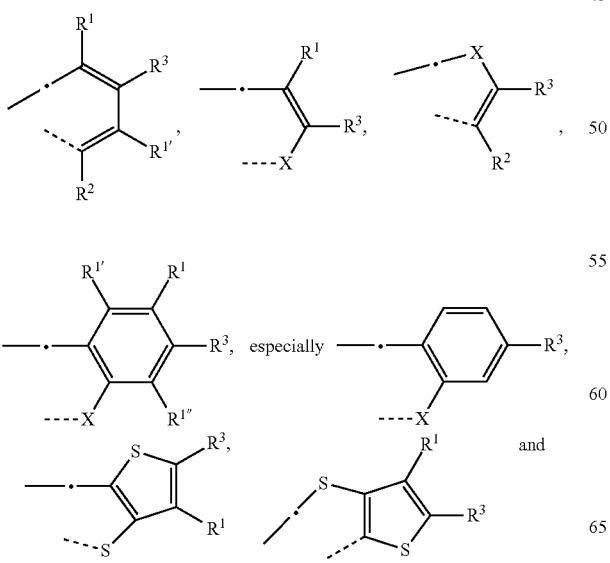

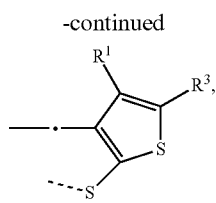

wherein the dotted lines denotes the bonds to the 6-membered ring (the dotted line —·— indicates the bond to the carbon atom in para-position to the nitrogen atom, the dotted line —————— indicates the bond to the carbon atom in meta-position to the nitrogen atom), $R^1$, $R^{1'}$ and $R^{1''}$ are independently of each other H, F, cyano, $C_1$-$C_{25}$alkoxy, $C_1$-$C_{25}$alkyl substituted with one or more halogen atoms, especially F; or $C_1$-$C_{25}$alkyl, $R^2$ is H, F, cyano, $C_1$-$C_{25}$alkoxy, or $C_1$-$C_{25}$alkyl, $R^3$ is hydrogen, F, cyano, $C_1$-$C_{25}$alkoxy, $C_1$-$C_{25}$alkyl substituted with one or more halogen atoms, especially F; $C_1$-$C_{25}$alkyl, -continued

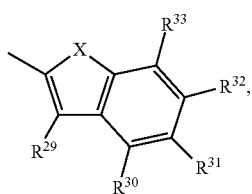

wherein $R^{22}$ to $R^{25}$ and $R^{29}$ to $R^{33}$ represent independently of each other H, F, cyano, $C_1$-$C_{25}$alkoxy, $C_1$-$C_{25}$alkyl substituted with one or more halogen atoms, especially F; or $C_1$-$C_{25}$alkyl, and $R^{26}$ is H, F, cyano, phenyl, $C_1$-$C_{25}$alkoxy, $C_1$-$C_{25}$alkyl substituted with one or more halogen atoms, or $C_1$-$C_{25}$alkyl;

X is O, S, Se, or $NR^4$, $R^4$ is hydrogen, $C_6$-$C_{18}$aryl; $C_6$-$C_{18}$aryl which is substituted by $C_1$-$C_8$ alkyl, or $C_1$-$C_{18}$alkoxy; $C_1$-$C_{25}$alkyl, which may optionally be interrupted by one or more oxygen or sulphur atoms and/or is optionally substituted by one or more halogen atoms, especially F; or $C_7$-$C_{25}$arylalkyl.

3. The compound according to claim 2, which is a compound of formula

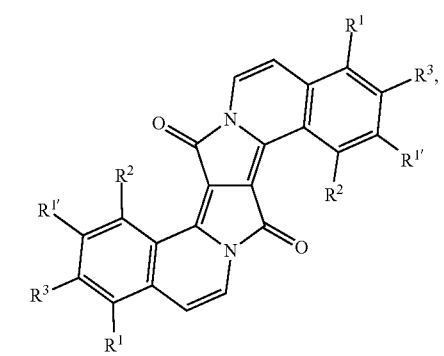
(IIIa)

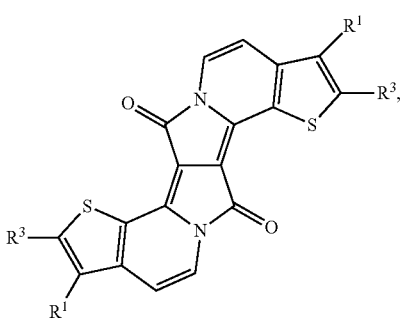
(IIIb)

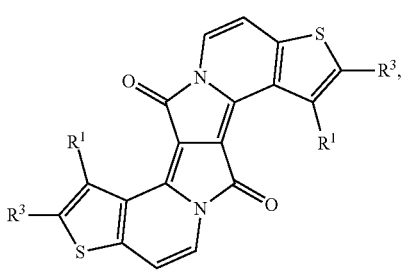
(IIIc)

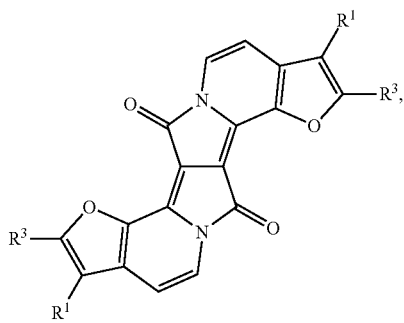
(IIId)

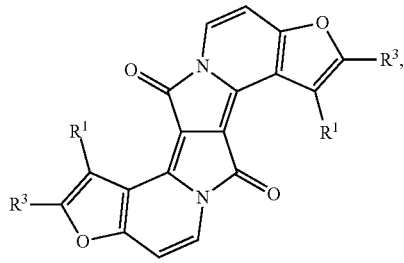
(IIIe)

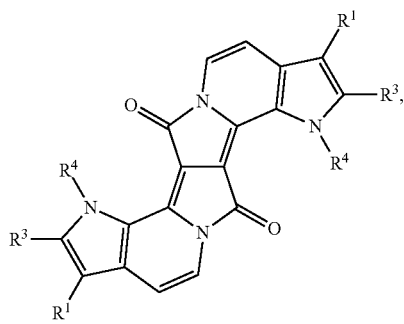
(IIIf)

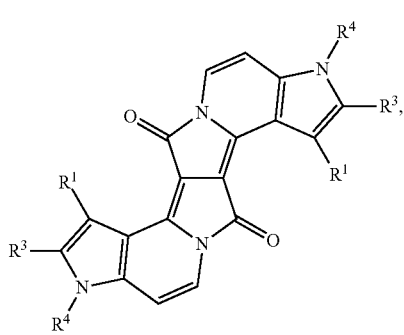
(IIIg)

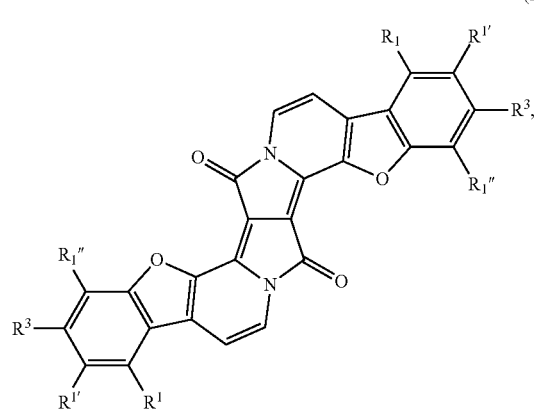
(IIIh)

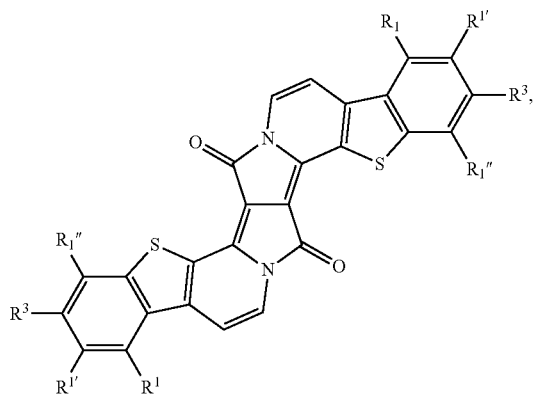
(IIIi)

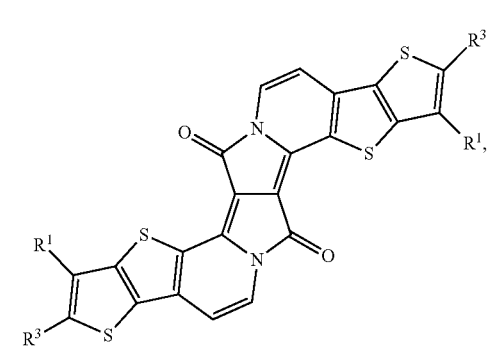
(IIIj)

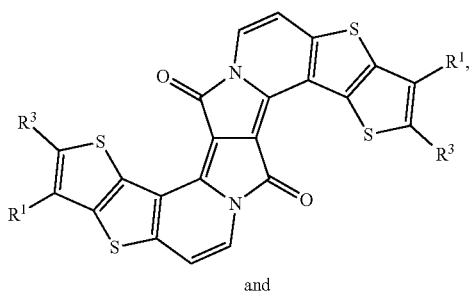
(IIIk)

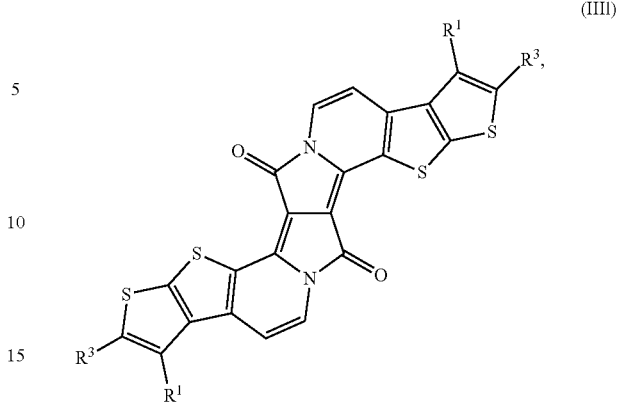
(IIIl)

especially (IIIa'), (IIIb') (IIIc'), (IIId'), (IIIe'), (IIIf'), (IIIg'), (IIIh'), (IIIi'), (IIIj'), (IIIk'), and (IIIl'), very especially (IIIa'), (IIIb'), (IIId'), (IIIf'), (IIIh'), (IIIi') and (IIIj'); wherein $R^1$, $R^{1'}$, $R^{1''}$, $R^2$, $R^3$ and $R^4$ are as defined in claim 2.

4. The compound according to claim 2, or 3, wherein $R^1$, $R^{1'}$, and $R^{1''}$ are independently of each other H, $C_1$-$C_{25}$alkoxy, or $C_1$-$C_{25}$alkyl, especially hydrogen, or $C_1$-$C_{25}$alkyl; very especially hydrogen.

5. The compound according to any of claims 2 to 4, wherein $R^2$ is H, $C_1$-$C_{25}$alkoxy, or $C_1$-$C_{25}$alkyl; especially hydrogen, or $C_1$-$C_{25}$alkyl, very especially hydrogen.

6. The compound according to any of claims 2 to 5, wherein $R^3$ is hydrogen, F, cyano, $C_1$-$C_{25}$alkyl,

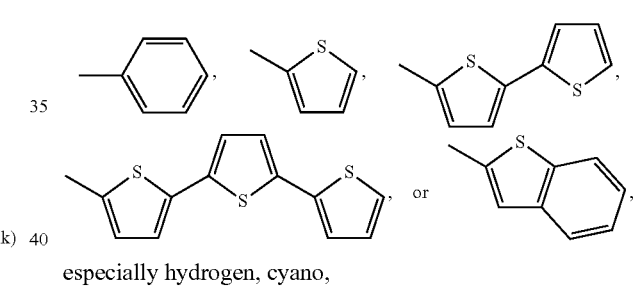

especially hydrogen, cyano,

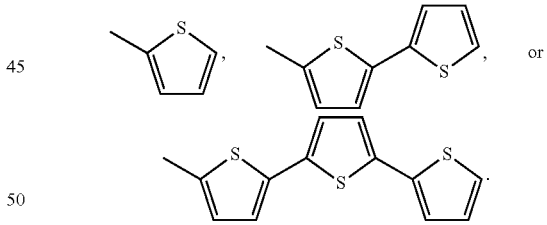

7. The compound according to any of claims 1 to 6, which is selected from

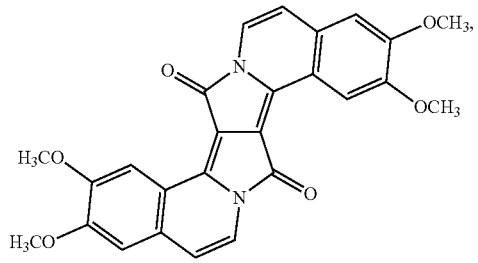
(3a)

and

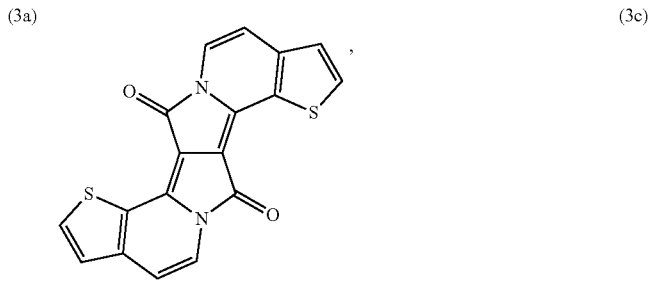
(3c)

-continued
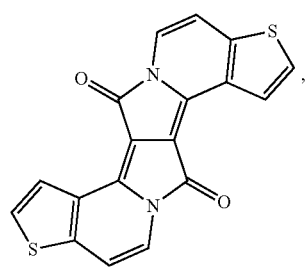
(3d)
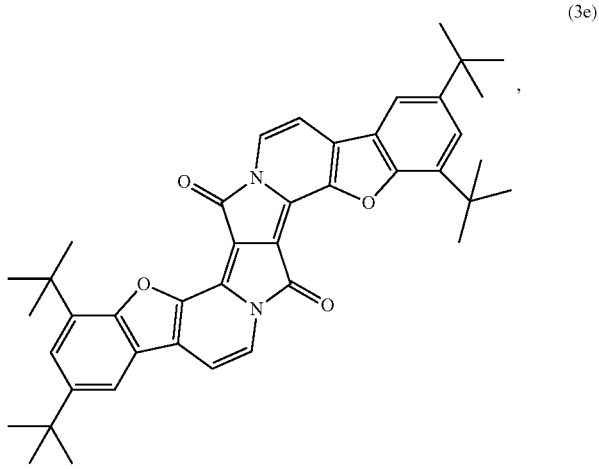
(3e)
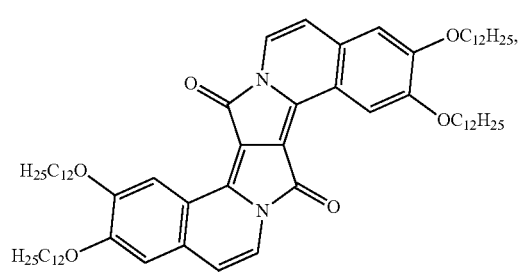
(3f)
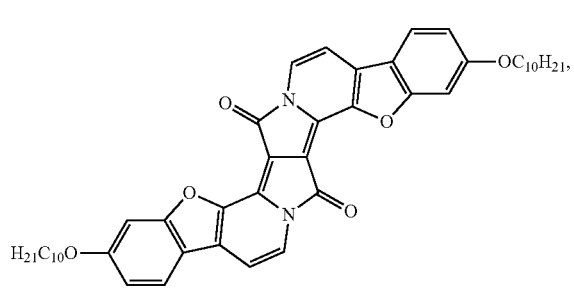
(3g)
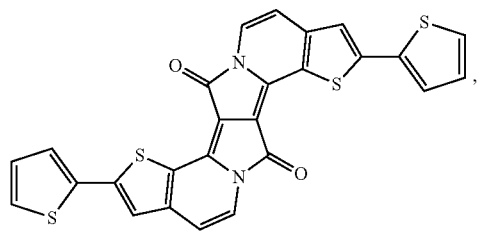
(4a)
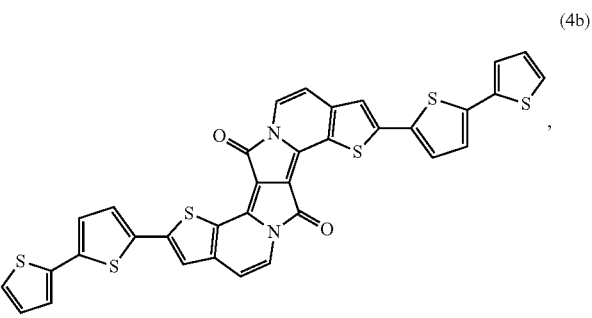
(4b)
and
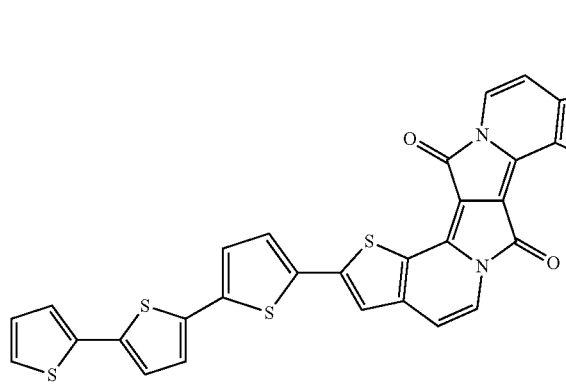
(4c)

8. A method for the production of a compound of formula (III):

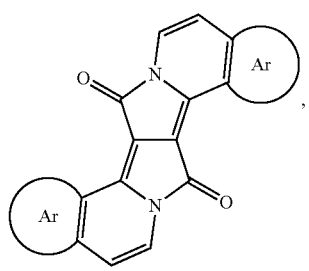

(III)

where Ar is as defined in claim 1, characterized in that a) a diketopyrrolopyrrole of formula (I):

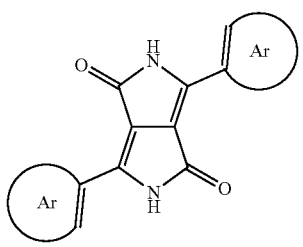

(I)

is alkylated in a reaction with an acetal, especially diethylacetal of bromoacetic aldehyde, and then b) the N-alkylated derivative of formula (II) obtained in step a)

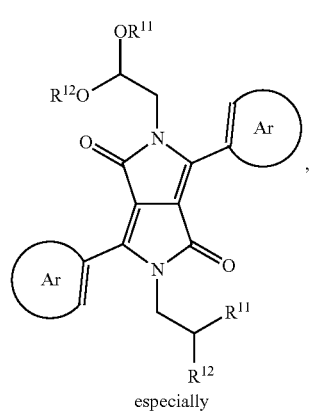

(II)

especially

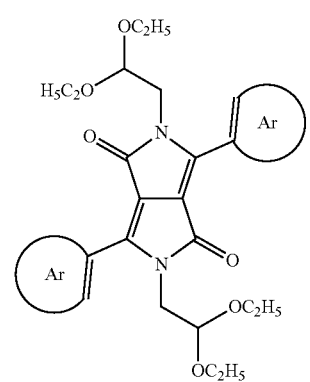

(II)

is submitted in the presence of acid to intramolecular condensation, obtaining the compound of formula (III), wherein $R^{11}$ and $R^{12}$ are $C_1$-$C_8$alkyl, or together form a ring

9. The method according to claim 8, characterized in that in step a) the alkylation reaction is carried out in the presence of tetrabutylammonium hydrogen sulfate, $K_2CO_3$ and dimethylformamide (DMF), and the product obtained is isolated from the reaction mixture by extraction.

10. The method according to claim 8, or 9, characterized in that in step b) the cyclization reaction is carried out in a mixture of ethanol and dioxane in the presence of HCl.

11. The method according to claim 8, or 9, characterized in that in step b) the cyclization reaction is carried out in methylene chloride in the presence of trifluoromethanesulphonic acid.

12. Use of the compounds of formula (III) according to any of claims 1 to 7 as organic pigment, the development of fluorometric techniques, in modern biomedical techniques and diagnostics, fluorescence imaging, detection of cations and colouring of artist's or industrial paints.

13. An organic semiconductor material, layer or component, comprising a compound according to any of claims 1 to 7.

14. A semiconductor device, comprising a compound according to according to any of claims 1 to 7, and/or an organic semiconductor material, layer or component according to claim 13.

15. The semiconductor device according to claim 14, which is an organic photovoltaic device, a photodiode, or an organic field effect transistor.

16. Process for the preparation of an organic semiconductor device, which process comprises applying a solution and/or dispersion of a compound according to any of claims 1 to 7 in an organic solvent to a suitable substrate and removing the solvent; or which process comprises evaporation of a compound according to any of claims 1 to 7.

17. A compound of formula

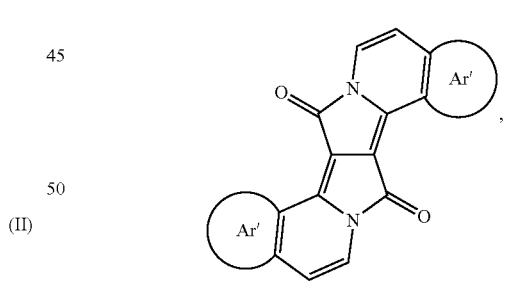

(V)

wherein Ar' denotes a homo- or heteroaromatic system, which is selected from

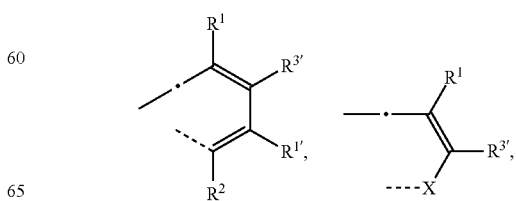

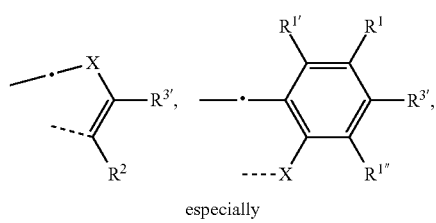

especially

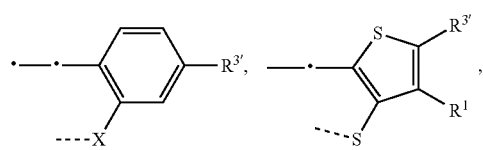

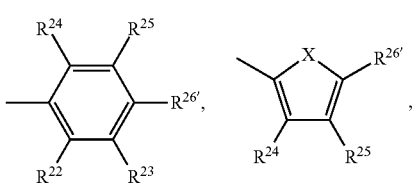 and 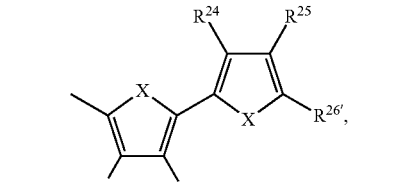

wherein the dotted lines denotes the bonds to the 6-membered ring (the dotted line ━ ･ ━ indicates the bond to the carbon atom in para-position to the nitrogen atom, the dotted line ━ ━ ━ ━ indicates the bond to the carbon atom in meta-position to the nitrogen atom), $R^1$, $R^{1'}$, $R^{1'''}$, $R^2$ and X are as defined in claim 2, $R^{3'}$ is Cl, Br, I,

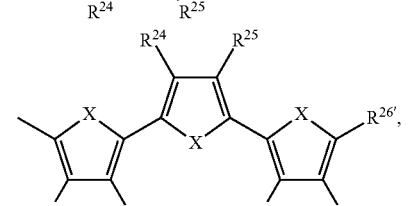
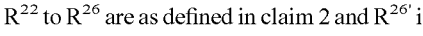

wherein $R^{22}$ to $R^{26}$ are as defined in claim 2 and $R^{26'}$ is Cl, Br, or I.

18. The compound according to claim 16, which is selected from

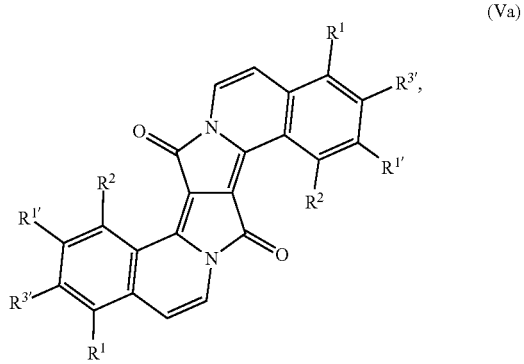 (Va)

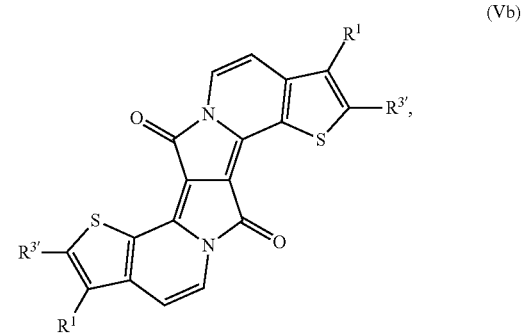 (Vb)

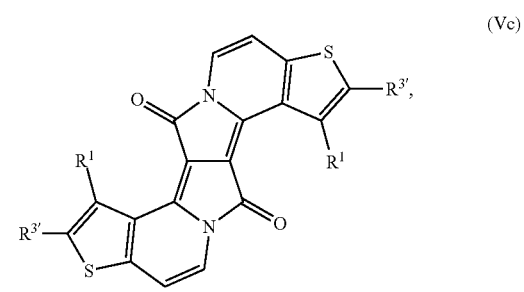 (Vc)

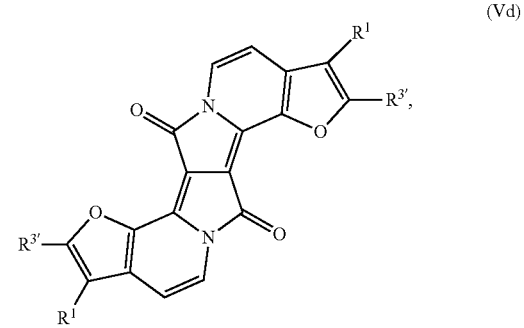 (Vd)

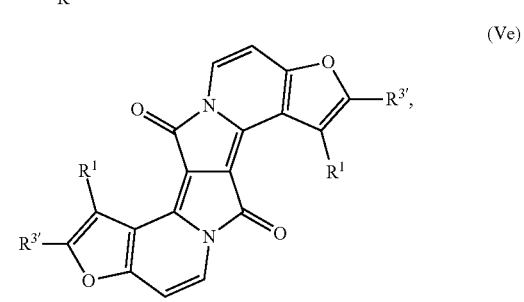 (Ve)

(Vf) 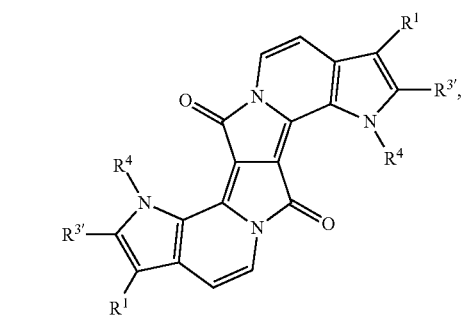
(Vg) 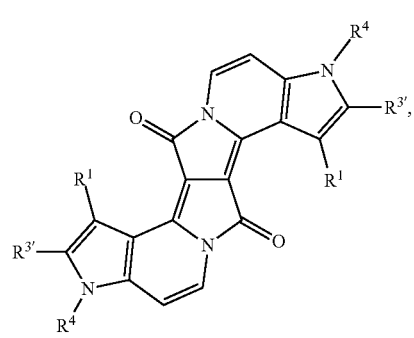
(Vh) 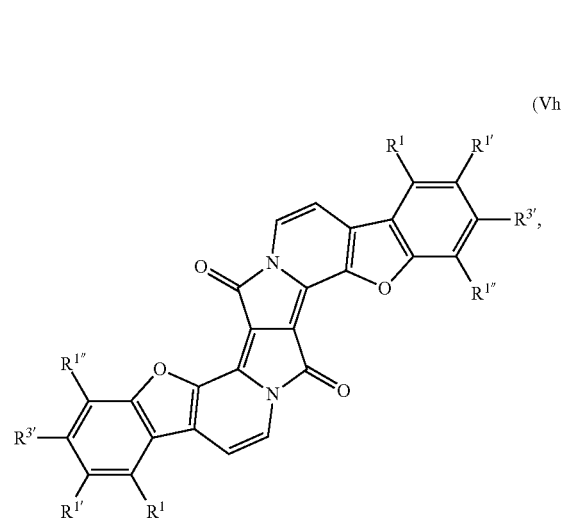
(Vi) 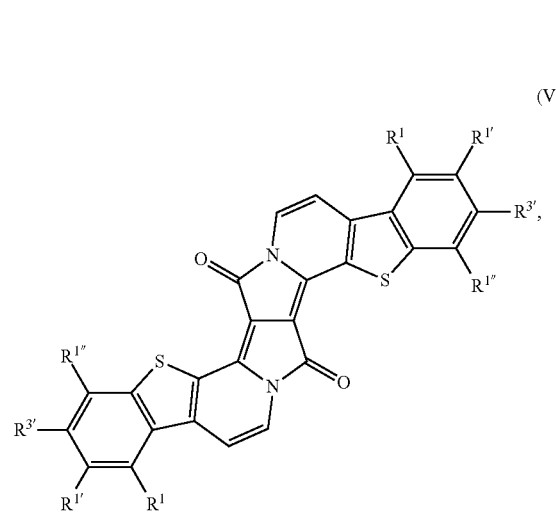
(Vj) 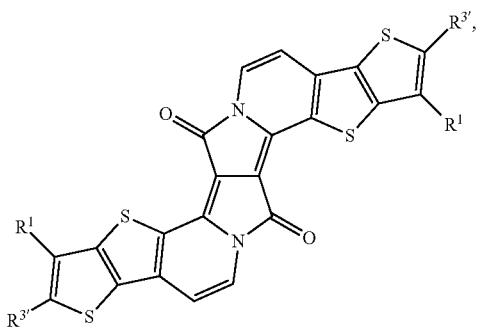
(Vk) 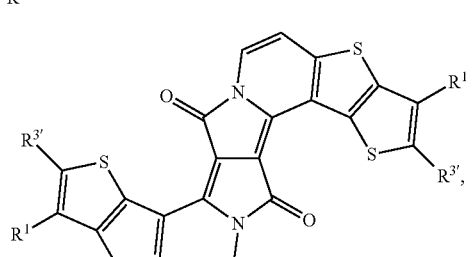
(Vl) 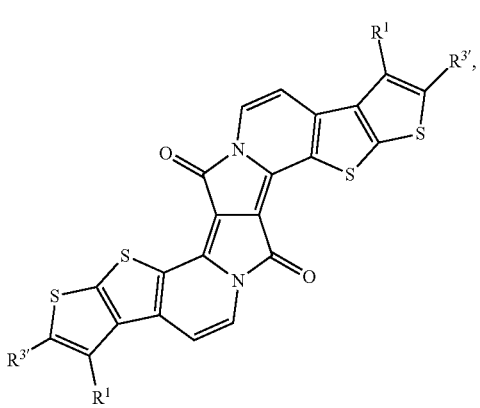
or
$R^1$, $R^{1'}$, $R^{1'''}$, $R^2$ and X are as defined in claim 2,
$R^{3'}$ is Cl, Br, I,
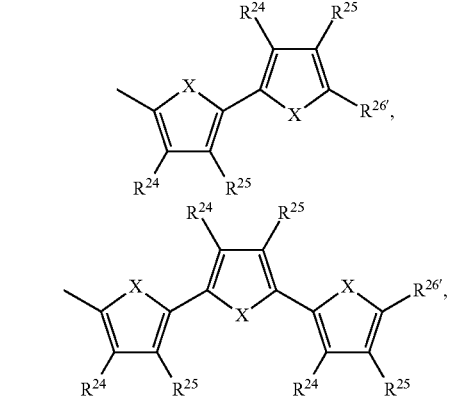

wherein $R^{22}$ to $R^{26}$ are as defined in claim 2 and $R^{26'}$ is Cl, Br, or I.
19. The compound according to claim 17, or 18, which is selected from
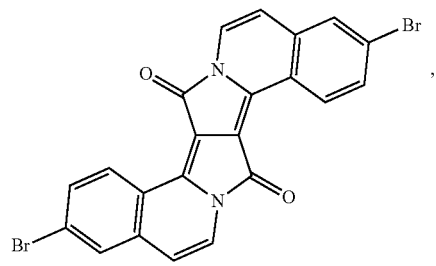
(3b)
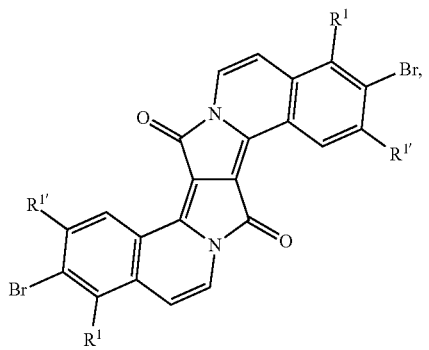
(5a)
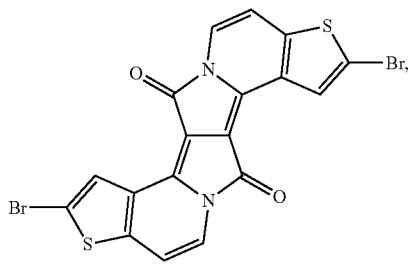
(5b)             (5c)
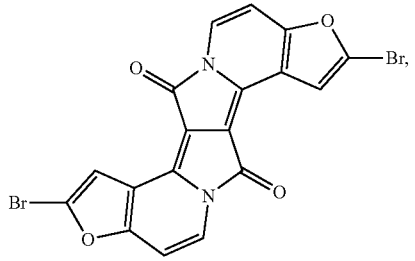
(5d)             (5e)
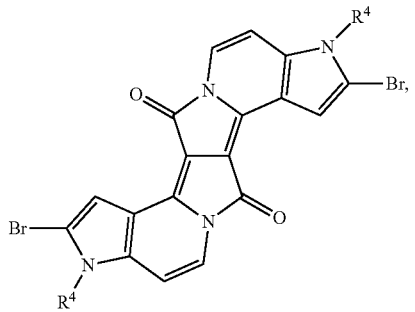
(5f)             (5g)
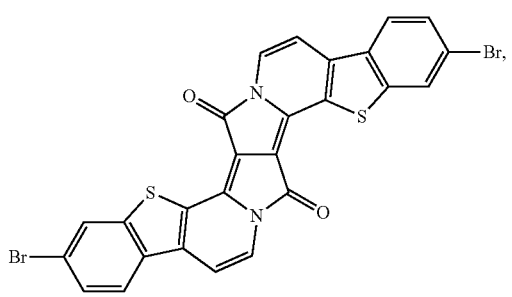
(5h)             (5i)

-continued

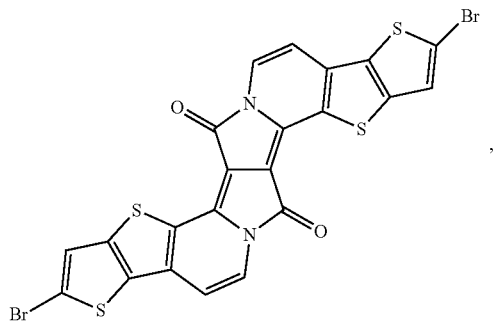
(5j)

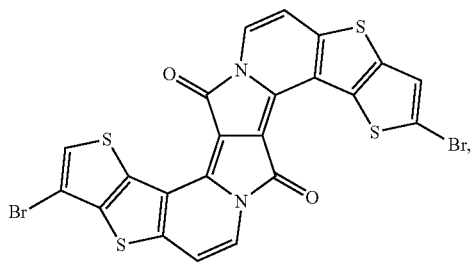
(5k)

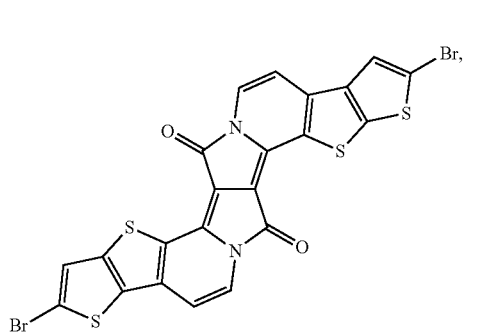
(5l)

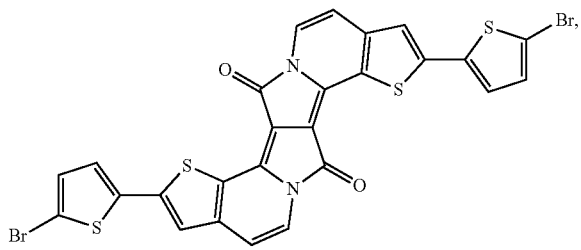
(5m)

and

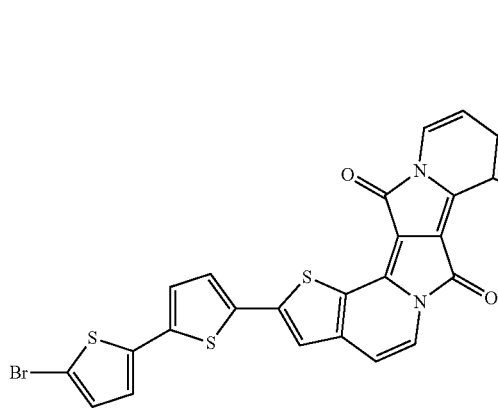
(5n)

wherein $R^1$ and $R^1$ are independently of each other hydrogen, or $C_1$-$C_{25}$alkyl, most preferred hydrogen.

20. Use of the compounds of any of claims 16 to 18 for the production of polymers, or in semiconductor devices, especially a sensor, a diode, a photodiode, an organic field effect transistor, a transistor for flexible displays, and/or a solar cell (photovoltaic cell).

The invention also relates to a method of production of a compound of formula (III):

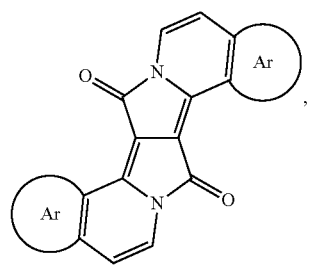
(III)

where Ar denotes a homo- or heteroaromatic system, characterized in that a) a diketopyrrollopyrrole of formula (I):

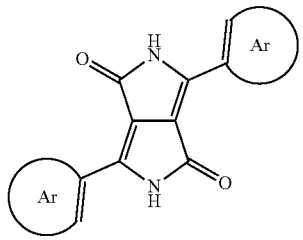

is alkylated in a reaction with diethylacetal of bromoacetic aldehyde, and then b) the N-alkylated derivative of formula (II) obtained in step a)

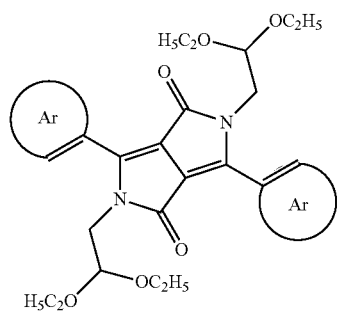

is submitted in the presence of acid to intramolecular condensation, obtaining the compound of formula (III).

The compounds of formula (I) are known, or can be prepared according to known procedures. Reference is made, for example, to WO2009047104, wherein in addition methods for halogenations as well as chain-extensions are described.

Preferably, in step a) the alkylation reaction is carried out in the presence of tetrabutylammonium hydrogen sulfate (TBAHS), $K_2CO_3$ and DMF, preferably at a temperature of 20-140° C., especially 90-130° C., very especially about 120° C., and the product obtained is isolated from the reaction mixture by extraction, preferably with aqueous solution of methylene chloride. Equally preferably, in step b) the cyclization reaction is carried out in a mixture of ethanol and dioxane in the presence of HCl. Equally preferably, in step b) the cyclization reaction is carried out in methylene chloride in the presence of trifluoromethanesulphonic acid. Instead of methylene chloride toluene, chlorobenzene, dichlorobenzene and sulfolane may be used.

The compounds according to the invention possess a number of advantageous properties. The dyes according to the invention are characterized by very strong absorption of radiation in the range 520-620 nm (the molar absorption coefficient of light is 80000-120000 units). This means that in any practical application, less substance can be used with the same end result. In addition, some of these dyes have very poor solubility both in water and in any organic solvents. Accordingly, they are pigments, which is very advantageous from the standpoint of application in the dyeing industry. The dyes according to the present invention also display very strong fluorescence of light in the range 570-630 nm. The fluorescence quantum yields range from 10 to 40%. The Stokes shift, an extremely important factor, is 200-240 $cm^{-1}$. This combination of favourable optical and photophysical features is unique. Owing to these features, these dyes are excellent candidates for application in such fields as: fluorescence imaging, detection of cations and colouring of artist's or industrial paints.

Method of Production of the Compounds According to the Invention

All the compounds of formula (III) can be obtained in a three-step synthesis according to one general scheme. In the first step, aromatic nitriles 0 were submitted, by a known method, to transformation to the diketopyrrolopyrroles (I) (DPP). The previously known diketopyrrolopyrroles (which are used as red pigments) were alkylated on the nitrogen atoms with diethylacetal of bromoacetic aldehyde, obtaining the so-called N-alkyl derivatives (II). These substances are then submitted in the presence of acid to intramolecular condensation of the Friedel-Crafts type, which leads to formation of the violet dyes and pigments (III) of previously unknown structure (Scheme 1).

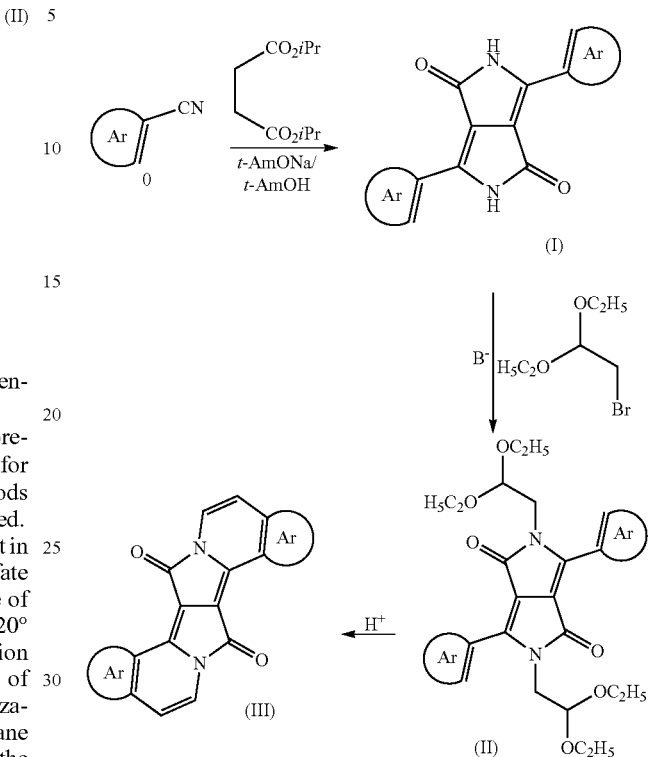

The method of production of the new compounds is simple in execution. The yield of the individual steps is good or very good. In many cases the final compounds can be isolated from the reaction mixture without using chromatography (in view of the low solubility in an aqueous medium).

A detailed description of the production of the compounds of formula (III) is given in the Examples that follow.

Halogen is fluorine, chlorine, bromine and iodine, especially fluorine.

$C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

A $C_1$-$C_{25}$alkyl group, which is substituted by one, or more halogen atoms, is a $C_1$-$C_{25}$alkyl group, wherein all, or part of the hydrogen atoms of the corresponding alkyl group have been replaced by halogen atoms, especially fluorine atoms, such as for example —$CF_3$, —$CF_2CF_3$, —$CF_2CF_2CF_3$, —$CF(CF_3)_2$, —$(CF_2)_3CF_3$, and —$C(CF_3)_3$.

$C_1$-$C_{25}$alkoxy ($C_1$-$C_{18}$alkoxy) groups are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, preferably $C_1$-$C_4$alkoxy such as typically methoxy, ethoxy, n-propoxy, isopropoxy, n-butoxy, sec.-butoxy, isobutoxy, tert.-butoxy. The term "alkylthio group" means the same groups as the alkoxy groups, except that the oxygen atom of the ether linkage is replaced by a sulfur atom.

The $C_7$-$C_{25}$arylalkyl groups can be substituted one to five times with $C_1$-$C_8$alkyl, $C_1$-$C_8$alkoxy, $CF_3$ and/or F. Examples are benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ω,ω-dim-ethyl-ω-phenyl-butyl, in which both the aliphatic hydrocarbon group and aromatic hydrocarbon group may be unsubstituted or substituted. Preferred examples are benzyl, 2-phenylethyl, 3-phenylpropyl, naphthylethyl, naphthylmethyl, and cumyl.

$C_6$-$C_{24}$aryl ($C_6$-$C_{18}$aryl) is typically phenyl, indenyl, azulenyl, naphthyl, biphenyl, asindacenyl, s-indacenyl, acenaphthylenyl, fluorenyl, phenanthryl, fluoranthenyl, triphenylenyl, chrysenyl, naphthacen, picenyl, perylenyl, pentaphenyl, hexacenyl, pyrenyl, or anthracenyl, preferably phenyl, 1-naphthyl, 2-naphthyl, 4-biphenyl, 9-phenanthryl, 2- or 9-fluorenyl, 3- or 4-biphenyl, which may be unsubstituted or substituted. Examples of $C_6$-$C_{12}$aryl are phenyl, 1-naphthyl, 2-naphthyl, 3- or 4-biphenyl, 2- or 9-fluorenyl or 9-phenanthryl, which may be unsubstituted or substituted.

Heteroaryl is typically $C_2$-$C_{20}$heteroaryl, i.e. a ring with five to seven ring atoms or a condensed ring system, wherein nitrogen, oxygen or sulfur are the possible hetero atoms, and is typically an unsaturated heterocyclic group with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl or phenoxazinyl, which can be unsubstituted or substituted.

Possible substituents of the above-mentioned aryl, or heteroaryl groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, a, a nitro group, or a silyl group, especially $C_1$-$C_8$alkyl, $C_1$-$C_8$alkoxy, $C_1$-$C_8$alkylthio, halogen, halo-$C_1$-$C_8$alkyl, or a cyano group.

$C_1$-$C_{25}$alkyl interrupted by one or more O is, for example, $(CH_2CH_2O)_{1-9}$—$R^x$, where $R^x$ is H or $C_1$-$C_{10}$alkyl, $CH_2$—$CH(OR^{y'})$—$CH_2$—O—$R^y$, where $R^y$ is $C_1$-$C_{18}$alkyl, and $R^{y'}$ embraces the same definitions as $R^y$ or is H. $C_1$-$C_{25}$alkyl interrupted by one or more S is, for example, $(CH_2CH_2S)_{1-9}$—$R^x$, where $R^x$ is H or $C_1$-$C_{10}$alkyl, $CH_2$—$CH(SR^{y'})$—$CH_2$—S—$R^y$, where $R^y$ is $C_1$-$C_{18}$alkyl, and $R^{y'}$ embraces the same definitions as $R^y$ or is H.

If a substituent, such as, for example, $R^{24}$, or $R^{25}$, occurs more than one time in a group, it can be different in each occurrence.

The homo- or heteroaromatic system (Ar) is selected from the group consisting of benzene, furan, thiopene, pyrrole, selenophene, benzofuran, benzothiophene, indole, benzoselenophene, thieno[2,3-b]thiophene and thieno[3,2-b]thiophene. The homo- or heteroaromatic system may be unsubstituted, or substituted. Examples of substituents are halogen, especially F; cyano, $C_1$-$C_{25}$alkoxy, $C_1$-$C_{25}$alkyl, $C_1$-$C_{25}$alkyl substituted with one or more halogen atoms, especially F;

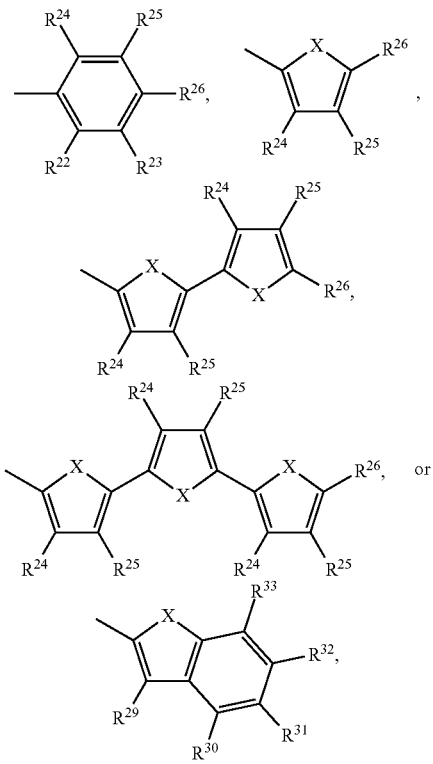

wherein $R^{22}$ to $R^{26}$ and $R^{29}$ to $R^{33}$ are as defined above.

The compounds of formula (III) may be used as functional dyes in dye sensitized and bulk heterojunction solar cells, organic light-emitting diodes, photodiodes, organic field-effect transistors, fluorescence imaging, sensors and solid-state dye lasers.

Advantageously, the compound of formula (III), or an organic semiconductor material, layer or component, comprising the compound of formula (III) can be used in organic photovoltaics (solar cells) and photodiodes, or in an organic field effect transistor (OFET).

A mixture containing the compound of formula (III) results in a semi-conducting layer comprising the compound of formula (III) (typically 0.1% to 99.9999% by weight, more specifically 1% to 99.9999% by weight, even more specifically 5% to 99.9999% by weight, especially 20 to 85% by weight) and at least another material. The other material can be, but is not restricted to another compound of formula (III), a semi-conducting polymer, a non-conductive polymer, organic small molecules, carbon nanotubes, a fullerene derivative, inorganic particles (quantum dots, quantum rods, quantum tripods, $TiO_2$, ZnO etc.), conductive particles (Au, Ag etc.), insulator materials like the ones described for the gate dielectric (PET, PS etc.).

Accordingly, the present invention also relates to an organic semiconductor material, layer or component, comprising a compound of formula (III) and to a semiconductor device, comprising a compound of formula (III) and/or an organic semiconductor material, layer or component. The semiconductor device is especially a sensor, a diode, a photodiode, an organic field effect transistor, a transistor for flexible displays, and/or a solar cell (photovoltaic cell).

The semiconductor is preferably an organic photovoltaic (PV) device (solar cell), a photodiode, or an organic field effect transistor. The structure and the components of the OPV and OFET device will be described in more detail below.

Accordingly, the invention provides organic photovoltaic (PV) devices (solar cells) comprising a compound of the formula (III).

The compound of formula (III) for use in an electronic device is preferably a compound of formula (IIIa), (IIIb), (IIId), (IIIf), (IIIg), (IIIh), (IIIi) and (IIIj), especially (IIIb), (IIId) and (IIIj); more preferably a compound of formula (IIIa'), (IIIb'), (IIId), (IIIf), (IIIg'), (IIIh'), (IIIi') and (IIIj'), very especially (IIIb'), (IIId') and (IIIj').

The structure of organic photovoltaic devices (solar cells) is, for example, described in C. Deibel et al. Rep. Prog. Phys. 73 (2010) 096401 and Christoph Brabec, Energy Environ. Sci 2. (2009) 347-303.

The PV device comprise in this order:
(a) a cathode (electrode),
(b) optionally a transition layer, such as an alkali halogenide, especially lithium fluoride, (c) a photoactive layer,
(d) optionally a smoothing layer,
(e) an anode (electrode),
(f) a substrate.

The photoactive layer comprises the compounds of the formula (III). Preferably, the photoactive layer is made of a compound of the formula (III), as an electron donor and an acceptor material, like a fullerene, particularly a functionalized fullerene PCBM, as an electron acceptor. As stated above, the photoactive layer may also contain a polymeric binder. The ratio of the small molecules of formula (III) to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA).

The fullerenes useful in this invention may have a broad range of sizes (number of carbon atoms per molecule). The term fullerene as used herein includes various cage-like molecules of pure carbon, including Buckminsterfullerene ($C_{60}$) and the related "spherical" fullerenes as well as carbon nanotubes. Fullerenes may be selected from those known in the art ranging from, for example, $C_{20}$-$C_{1000}$. Preferably, the fullerene is selected from the range of $C_{60}$ to $C_{96}$. Most preferably the fullerene is $C_{60}$ or $C_{70}$, such as [60]PCBM, or [70]PCBM. It is also permissible to utilize chemically modified fullerenes, provided that the modified fullerene retains acceptor-type and electron mobility characteristics. The acceptor material can also be a material selected from the group consisting of another compounds of formula III, or any semi-conducting polymer, provided that the polymers retain acceptor-type and electron mobility characteristics, organic small molecules, carbon nanotubes, inorganic particles (quantum dots, quantum rods, quantum tripods, $TiO_2$, ZnO etc.).

The photoactive layer is made of a compound of the formula (III) as an electron donor and a fullerene, particularly functionalized fullerene PCBM, as an electron acceptor. These two components are mixed with a solvent and applied as a solution onto the smoothing layer by, for example, the spin-coating method, the drop casting method, the Langmuir-Blodgett ("LB") method, the ink jet printing method and the dripping method. A squeegee or printing method could also be used to coat larger surfaces with such a photoactive layer. Instead of toluene, which is typical, a dispersion agent such as chlorobenzene is preferably used as a solvent. Among these methods, the vacuum deposition method, the spin-coating method, the ink jet printing method and the casting method are particularly preferred in view of ease of operation and cost.

In the case of forming the layer by using the spin-coating method, the casting method and ink jet printing method, the coating can be carried out using a solution and/or dispersion prepared by dissolving, or dispersing the composition in a concentration of from 0.01 to 90% by weight in an appropriate organic solvent such as benzene, toluene, xylene, tetrahydrofurane, methyltetrahydrofurane, N,N-dimethylformamide, acetone, acetonitrile, anisole, dichloromethane, dimethylsulfoxide, chlorobenzene, 1,2-dichlorobenzene and mixtures thereof.

The photovoltaic (PV) device can also consist of multiple junction solar cells that are processed on top of each other in order to absorb more of the solar spectrum. Such structures are, for example, described in App. Phys. Let. 90, 143512 (2007), Adv. Funct. Mater. 16, 1897-1903 (2006) and WO2004/112161.

A so called 'tandem solar cell' comprise in this order:
(a) a cathode (electrode),
(b) optionally a transition layer, such as an alkali halogenide, especially lithium fluoride, (c) a photoactive layer,
(d) optionally a smoothing layer,
(e) a middle electrode (such as Au, Al, ZnO, $TiO_2$ etc.)
(f) optionally an extra electrode to match the energy level,
(g) optionally a transition layer, such as an alkali halogenide, especially lithium fluoride,
(h) a photoactive layer,
(i) optionally a smoothing layer,
(j) an anode (electrode),
(k) a substrate. The compound of formula (III) is comprised by at least one of the photoactive layers.

The PV device can also be processed on a fiber as described, for example, in US20070079867 and US 20060013549.

Due to their excellent self-organising properties the materials or films comprising the compounds of the formula (III) can also be used alone or together with other materials in or as alignment layers in LCD or OLED devices, as described for example in US2003/0021913.

An OFET device according to the present invention preferably comprises:
a source electrode,
a drain electrode,
a gate electrode,
a semiconducting layer,
one or more gate insulator layers, and
optionally a substrate, wherein the semiconductor layer comprises a compound of formula (III).

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

Preferably the OFET comprises an insulator having a first side and a second side, a gate electrode located on the first side of the insulator, a layer comprising a compound of formula III located on the second side of the insulator, and a drain electrode and a source electrode located on the polymer layer.

The OFET device can be a top gate device or a bottom gate device.

Suitable structures and manufacturing methods of an OFET device are known to the skilled in the art and are described in the literature, for example in WO03/052841.

Typically the semiconducting layer of the present invention is at most 1 micron (=1 μm) thick, although it may be thicker if required. For various electronic device applications, the thickness may also be less than about 1 micron. For example, for use in an OFET the layer thickness may typically be 100 nm or less. The exact thickness of the layer will depend, for example, upon the requirements of the electronic device in which the layer is used.

The insulator layer (dielectric layer) generally can be an inorganic material film or an organic polymer film. Illustrative examples of inorganic materials suitable as the gate dielectric layer include silicon oxide, silicon nitride, aluminum oxide, barium titanate, barium zirconium titanate and the like. Illustrative examples of organic polymers for the gate dielectric layer include polyesters, polycarbonates, poly(vinyl phenol), polyimides, polystyrene, poly(methacrylate)s, poly(acrylate)s, epoxy resin, photosensitive resists as described in WO07/113,107 and the like. In the exemplary embodiment, a thermally grown silicon oxide ($SiO_2$) may be used as the dielectric layer.

The thickness of the dielectric layer is, for example from about 10 nanometers to about 2000 nanometers depending on the dielectric constant of the dielectric material used. A representative thickness of the dielectric layer is from about 100 nanometers to about 500 nanometers. The dielectric layer may have a conductivity that is for example less than about $10^{-12}$ S/cm.

The gate insulator layer may comprise for example a fluoropolymer, like e.g. the commercially available Cytop 809M®, or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. $FC_{75}$® (available from Acros, catalogue number 12380). Other suitable fluoropolymers and fluorosolvents are known in prior art, like for example the perfluoropolymers Teflon AF® 1600 or 2400 (from DuPont), or Fluoropel® (from Cytonix) or the perfluorosolvent FC 43® (Acros, No. 12377).

In the gate electrode and the source/drain electrodes included in the OFET of the present invention, a typical metal may be used, specific examples thereof include, but are not limited to, platinum (Pt), palladium (Pd), gold (Au), silver (Ag), copper (Cu), aluminum (Al), nickel (Ni). Alloys and oxides, such as molybdenum trioxide and indium tin oxide (ITO), may also be used. Preferably, the material of at least one of the gate, source and drain electrodes is selected from the group Cu, Ag, Au or alloys thereof. The source and drain electrodes may be deposited by thermal evaporation and patterned using standard photolithography and lift off techniques as are known in the art.

The substrate may be rigid or flexible. Rigid substrates may be selected from glass or silicon and flexible substrates may comprise thin glass or plastics such as poly (ethylene terephthalate) (PET), polyethylenenaphthalate (PEN), polycarbonate, polycarbonate, polyvinylalcohol, polyacrylate, polyimide, polynorbornene, and polyethersulfone (PES).

Alternatively, conductive polymers may be deposited as the source and drain electrodes. An example of such a conductive polymers is poly(ethylene dioxythiophene) (PEDOT) although other conductive polymers are known in the art. Such conductive polymers may be deposited from solution using, for example, spin coating or ink jet printing techniques and other solution deposition techniques.

The source and drain electrodes are preferably formed from the same material for ease of manufacture. However, it will be appreciated that the source and drain electrodes may be formed of different materials for optimisation of charge injection and extraction respectively.

Typical thicknesses of source and drain electrodes are about, for example, from about 40 nanometers to about 1 micrometer with the more specific thickness being about 100 to about 400 nanometers.

The length of the channel defined between the source and drain electrodes may be up to 500 microns, but preferably the length is less than 200 microns, more preferably less than 100 microns, most preferably less than 20 microns.

Other layers may be included in the device architecture. For example, a self assembled monolayer (SAM) may be deposited on the gate, source or drain electrodes, substrate, insulating layer and organic semiconductor material to promote crystallity, reduce contact resistance, repair surface characteristics and promote adhesion where required. Exemplary materials for such a monolayer include chloro- or alkoxy-silanes with long alkyl chains, eg octadecyltrichlorosilane.

In a preferred embodiment, the deposition of at least one compound of the general formula (III) (and if appropriate further semiconductor materials) is carried out by a gas phase deposition process (physical vapor deposition, PVD). PVD processes are performed under high-vacuum conditions and comprise the following steps: evaporation, transport, deposition. It has been found that, surprisingly, the compounds of the general formula (III) are suitable particularly advantageously for use in a PVD process, since they essentially do not decompose and/or form undesired by-products. The material deposited is obtained in high purity. In a specific embodiment, the deposited material is obtained in the form of crystals or comprises a high crystalline content. In general, for the PVD, at least one compound of the general formula III is heated to a temperature above its evaporation temperature and deposited on a substrate by cooling below the crystallization temperature. The temperature of the substrate in the deposition is preferably within a range from about 20 to 250° C., more preferably from 50 to 200° C.

The resulting semiconductor layers generally have a thickness which is sufficient for ohmic contact between source and drain electrodes. The deposition can be effected under an inert atmosphere, for example under nitrogen, argon or helium. The deposition is effected typically at ambient pressure or under reduced pressure. A suitable pressure range is from about $10^{-7}$ to 1.5 bar.

The compound of the formula (III) is preferably deposited on the substrate in a thickness of from 10 to 1000 nm, more preferably from 15 to 250 nm. In a specific embodiment, the compound of the formula (III) is deposited at least partly in crystalline form. For this purpose, especially the above-described PVD process is suitable. Moreover, it is possible to use previously prepared organic semiconductor crystals. Suitable processes for obtaining such crystals are described by R. A. Laudise et al. in "Physical Vapor Growth of Organic Semi-Conductors", Journal of Crystal Growth 187 (1998), pages 449-454, and in "Physical Vapor Growth of Centimeter-sized Crystals of α-Hexathiophene", Journal of Crystal Growth 1982 (1997), pages 416-427, which are incorporated here by reference.

OFETs have a wide range of possible applications. One such application is to drive pixels in an optical device (apparatus), preferably an organic optical device. Examples of such optical devices include photoresponsive devices, in particular photodetectors, and lightemissive devices, in particular organic light emitting devices. High mobility OTFTs are particularly suited as backplanes for use with active matrix organic light emitting devices, e.g. for use in display applications.

High efficiency of energy conversion, excellent field-effect mobility, high open-circuit voltages ($V_{oc}$), good on/off current ratios and/or excellent stability can be observed, when the according to the invention are used in organic field effect transistors, organic photovoltaics (solar cells) and photodiodes.

The following examples are included for illustrative purposes only and do not limit the scope of the claims. Unless otherwise stated, all parts and percentages are by weight.

EXAMPLES

1. Synthesis of Nitriles 5,7-Di-t-butylbenzofurano-2-carbonitrile (0e)

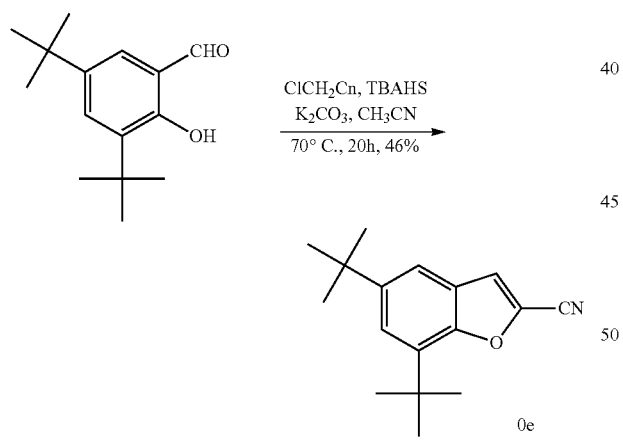

A mixture consisting of 3,5-di-t-butyl-2-hydroxybenzaldehyde (10.54 g, 45 mmol), chloroacetonitrile (3.4 ml, 54 mmol), tetrabutylammonium hydrogen sulphate (TBAHS, 0.78 g, 2.3 mmol), potassium carbonate (31.10 g, 225 mmol) and 270 ml acetonitrile was stirred at 70° C. The progress of the reaction was monitored using TLC. After complete conversion of the aldehyde was confirmed (about 30 h), the mixture was cooled and was diluted with water and methylene chloride. The aqueous phase was neutralized with acetic acid and extracted with three portions of methylene chloride. The combined organic phases were washed with water and brine and dried over anhydrous sodium sulphate. The solvents were evaporated, and the product was isolated on a chromatographic column (hexane:ethyl acetate 29:1). 5.17 g (45%) of crude 5,7-di-t-butylbenzofurano-2-carbonitrile was obtained as a brown solid, which can be used in the next steps without additional purification. If higher purity is required, the product can be recrystallized from ethanol. M.p.: 79-80° C. $^1$H-NMR (600 MHz, CDCl$_3$): δ 7.47 (d, J=1.8 Hz, 1H), 7.46 (d, J=1.8 Hz, 1H), 7.41 (s, 1H), 1.50 (s, 9H), 1.37 (s, 9H). $^{13}$C-NMR (150 MHz, CDCl$_3$): δ 152.6, 147.7, 135.0, 126.4, 125.8, 123.3, 118.8, 116.1, 112.4, 35.0, 34.6, 31.7, 29.7. HRMS (EI 70 eV) calc. for C$_{17}$H$_{21}$NO (M$^+$): 255.1623, found: 255.1626. Calc. elem. anal. (%) for the formula C$_{17}$H$_{21}$NO: C, 79.96; H, 8.29; N, 5.49. found: C, 79.74; H, 8.19; N, 5.47.

2. General Method of Synthesis of DPP (1a-g)

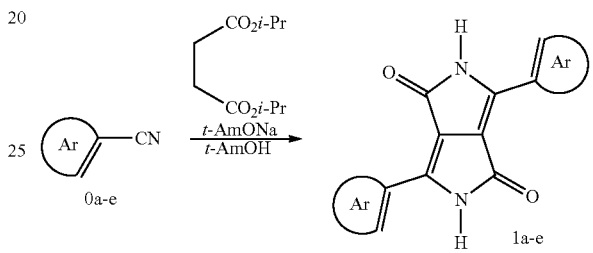

A three-necked flask equipped with a reflux condenser and magnetic stirrer was charged with 40 ml of tert-amyl alcohol, 1.15 g of sodium (50 mmol) and a catalytic amount of iron (III) chloride. The mixture was heated at the boiling point until the sodium had reacted completely. Then the reaction mixture was cooled to 90° C. and 23 mmol of nitrile was added with a syringe (solid nitriles should be dissolved beforehand in a small amount of tert-amyl alcohol). The mixture was heated to 110° C. and 2.1 ml (10 mmol) of diisopropyl succinate was added dropwise in the space of 30 min. After reaction at 110° C. for 16 h, the flask contents were cooled and 100 ml of a mixture of water, methanol and acetic acid in volumetric proportions 1:1:1 was added. The suspension obtained was heated for some minutes at the boiling point and then cooled to 30° C. The precipitate was filtered off, washed several times with hot water and methanol and dried under reduced pressure.

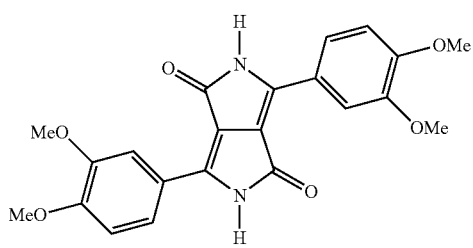 [SMILES: COc1ccc(C2=C3C(=O)NC(c4ccc(OC)c(OC)c4)=C3C(=O)N2)cc1OC]

2.1 1,4-Diketo-3,6-di(3,4-dimethoxyphenyl)pyrrolo[3,4-c]pyrrole (1a)

Obtained from 3,4-dimethoxybenzonitrile (0a) (3.75 g, 23 mmol). Yield: 736 mg (18%). Red powder. M.p.: Decomposition>370° C. $^1$H-NMR (500 MHz, DMSO-d$_6$, 80° C.): δ 10.84 (s, 2H), 8.18 (d, J=2.0 Hz, 2H), 8.10 (dd, J$_1$=2.0 Hz, $J_2$=8.4 Hz, 2H), 7.11 (d, J=8.4 Hz, 2H), 3.88 (s, 6H)), 3.86 (s, 6H). $^{13}$C-NMR (125 MHz, DMSO-$d_6$): δ 163.0, 152.5, 149.7, 143.7, 122.4, 121.5, 112.8, 112.4, 109.9, 56.5, 56.4. HRMS (EI 70 eV) calc. for $C_{22}H_{20}N_2O_6$ (M$^+$): 408.1321, found: 408.1316. Calc. elem. anal. (%) for the formula $C_{22}H_{20}N_2O_6$: C, 64.70; H, 4.94; N, 6.86. found: C, 64.64; H, 4.99; N, 6.62.

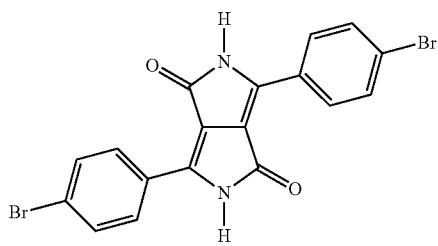 [SMILES: O=C1NC(c2ccc(Br)cc2)=C2C(=O)NC(c3ccc(Br)cc3)=C12]

2.2 1,4-Diketo-3,6-di(4-bromophenyl)pyrrolo[3,4-c]pyrrole (1b)

Obtained from 4-bromobenzonitrile (Ob) (4.19 g, 23 mmol). Yield: 3.28 g (74%). Red powder. M.p.: >400° C.

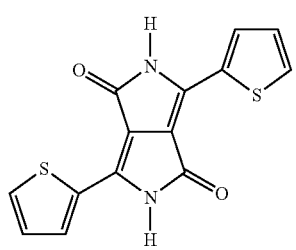 [SMILES: O=C1NC(c2cccs2)=C2C(=O)NC(c3cccs3)=C12]

2.3 1,4-Diketo-3,6-di(2-thiophenyl)pyrrolo[3,4-c]pyrrole (1c)

Obtained from thiopheno-2-carbonitrile (0c) (2.51 g, 23 mmol). Yield: 2.55 g (85%). Brown powder. M.p.: >380° C.

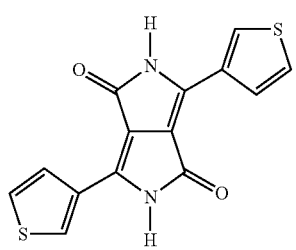 [SMILES: O=C1NC(c2ccsc2)=C2C(=O)NC(c3ccsc3)=C12]

2.4 1,4-Diketo-3,6-di(3-thiophenyl)pyrrolo[3,4-c]pyrrole (1d)

Obtained from thiopheno-3-carbonitrile (Od) (2.51 g, 23 mmol). Yield: 1.42 g (47%). Bright red powder. M.p.: >400° C. $^1$H-NMR (600 MHz, DMSO-$d_6$, 80° C.): δ 10.89 (s, 2H), 8.62 (s, 2H), 8.12 (s, 2H), 7.69 (s, 2H). HRMS (EI 70 eV) calc. for $C_{14}H_8N_2O_2S_2$ (M$^+$): 300.0027, found: 300.0018. Calc. elem. anal. (%) for the formula $C_{14}H_8N_2O_2S_2$: C, 55.98, H, 2.68, N, 9.33. found: C, 56.15; H, 2.64; N, 9.31.

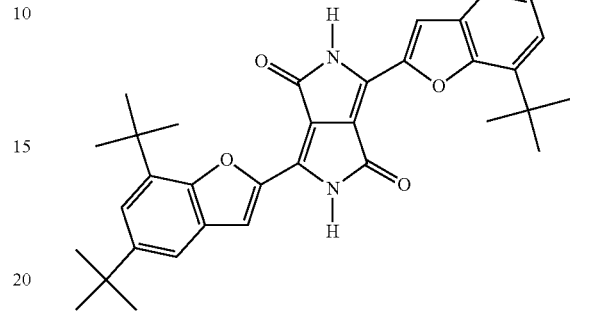

2.5 1,4-Diketo-3,6-di(5,7-di-t-butyl-2-benzofuryl)pyrrolo[3,4-c]pyrrole (1e)

Obtained from 5,7-di-t-butylbenzofurano-2-carbonitrile (0e) (5.87 g, 23 mmol). The residue obtained after filtration was dissolved in hot DMF, precipitated by adding ethanol, filtered off and dried. Yield: 4.71 g (79%). Violet powder. M.p.: >380° C. HRMS (EI 70 eV) calc. for $C_{38}H_{44}N_2O_4$ (M$^+$): 592.3301, found: 592.3308.

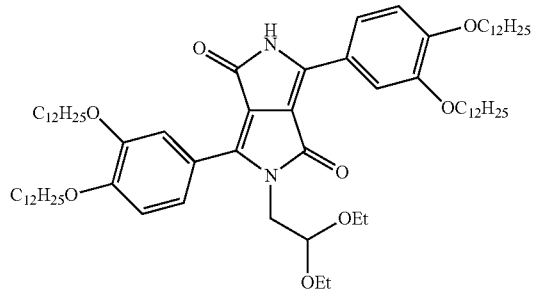

2.6 1,4-Diketo-3,6-di(3,4-didecyloxyphenyl)pyrrolo[3,4-c]pyrrole (1f)

Yield 34%.

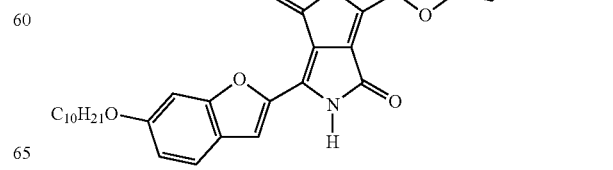

2.7 1,4-Diketo-3,6-di(6-decyloxy-2-benzofuryl)pyrrolo[3,4-c]pyrrole (1g):

Yield 81%

3. General Method of Synthesis of Diacetals 2a-g

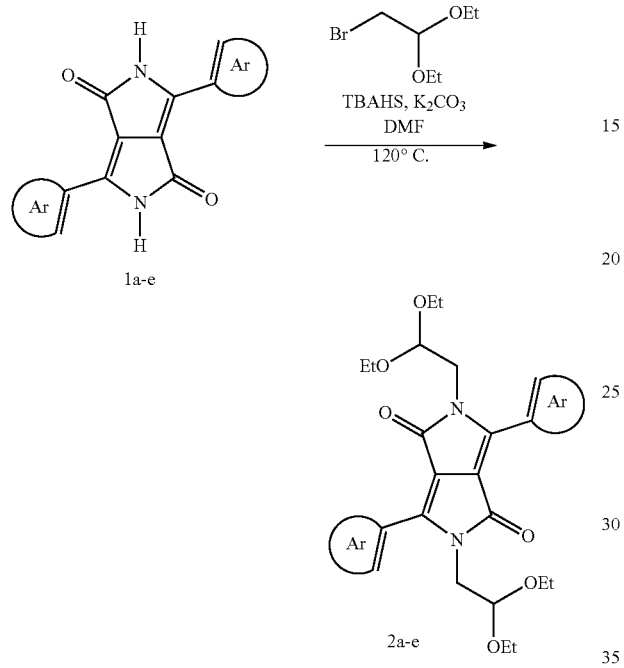

A mixture of pigment 1 (5 mmol), tetrabutylammonium hydrogen sulphate (TBAHS, 85 mg, 0.25 mmol), potassium carbonate (7.60 g, 55 mmol) and 120 ml DMF was heated to 120° C. in an argon atmosphere. Then diethylacetal of bromoacetaldehyde (7.5 ml, 55 mmol) was added dropwise using a syringe (30 min). The flask contents were stirred for the indicated time, cooled and diluted with water and methylene chloride. The aqueous phase was extracted with methylene chloride, the combined organic phases were washed with water and brine, and dried over anhydrous sodium sulphate. The solvents were evaporated, and the product was isolated on a chromatographic column in the indicated elution system.

3.1 2,5-Di(2,2-diethoxyethyl)-1,4-diketo-3,6-di(3,4-dimethoxyphenyl)pyrrolo[3,4-c]pyrrole (2a)

Obtained from 1a (2.04 g, 5 mmol). Reaction time: 24 h. Purified on a chromatographic column (methylene chloride:acetone 39:1→9:1). Yield: 1.61 g (48%). Orange powder. M.p.: ° C. $^1$H-NMR (500 MHz, CDCl$_3$): δ 7.82 (d, J=2.0 Hz, 2H), 7.79 (dd, J$_1$=2.0 Hz, J$_2$=8.4 Hz, 2H), 7.00 (d, J=8.4 Hz, 2H), 4.98 (t, J=5.8 Hz, 2H), 3.98 (s, 6H), 3.95 (s, 6H), 3.90 (d, J=5.8 Hz, 4H), 3.77-3.71 (m, 4H), 3.58-3.52 (m, 4H), 1.17 (t, J=7.1 Hz, 12H). $^{13}$C-NMR (125 MHz, CDCl$_3$): δ 163.5, 151.5, 148.9, 148.5, 123.7, 120.5, 112.7, 111.0, 108.5, 100.8, 64.3, 56.3, 56.0, 45.9, 15.4. HRMS (FD-TOF) calc. for C$_{34}$H$_{44}$N$_2$O$_{10}$ (M$^+$): 640.2996, found: 640.3006. Calc. elem. anal. (%) for the formula C$_{34}$H$_{44}$N$_2$O$_{10}$: C, 63.74, H, 6.92, N, 4.37. found: C, 63.72; H, 6.88; N, 4.30.

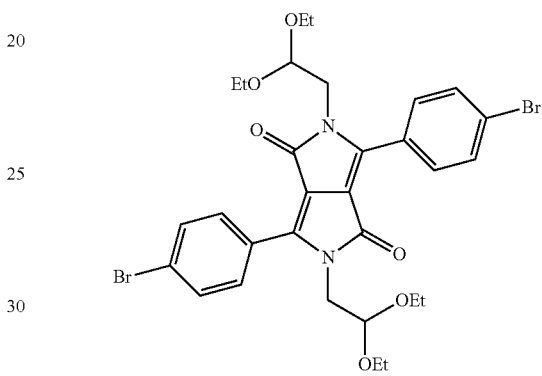

3.2 2,5-Di(2,2-diethoxyethyl)-1,4-diketo-3,6-di(4-bromophenyl)pyrrolo[3,4-c]pyrrole (2b)

Obtained from 1b (2.23 g, 5 mmol). Reaction time: 20 h at 120° C., 5 h at 140° C. Purified on a chromatographic column (methylene chloride:acetone 99:1). Yield: 916 mg (27%). Reddish-orange solid. M.p.: 198-201° C. $^1$H-NMR (500 MHz, CDCl$_3$): δ 7.96 (m, 4H), 7.65 (m, 4H), 4.86 (t, J=5.6 Hz, 2H), 3.80 (d, J=5.6 Hz, 4H), 3.76-3.69 (m, 4H), 3.55-3.48 (m, 4H), 1.16 (t, J=7.1 Hz, 12H). $^{13}$C-NMR (125 MHz, CDCl$_3$): δ 163.0, 148.4, 148.9, 132.1, 131.0, 126.6, 126.0, 109.4, 100.5, 64.3, 45.5, 15.3. HRMS (ESI) calc. for C$_{30}$H$_{34}$N$_2$O$_6$NaBr$_2$ (M+Na$^+$): 699.0676, found: 699.0684. Calc. elem. anal. (%) for the formula C$_{30}$H$_{34}$N$_2$O$_6$Br$_2$: C, 53.11; H, 5.05; N, 4.13. found: C, 52.95; H, 4.93; N, 4.09.

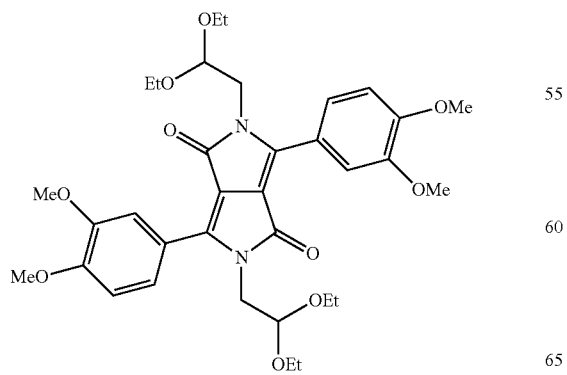

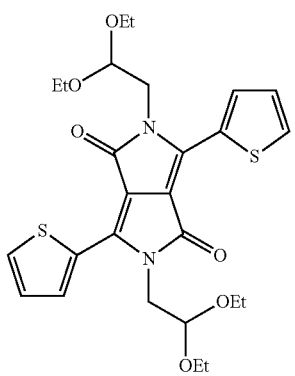 [SMILES: CCOC(CN1C(=O)C2=C(c3cccs3)N(CC(OCC)OCC)C(=O)C2=C1c1cccs1)OCC]

3.3 2,5-Di(2,2-diethoxyethyl)-1,4-diketo-3,6-di(2-thiophenyl)pyrrolo[3,4-c]pyrrole (2c)

Obtained from 1c (1.50 g, 5 mmol). Reaction time: 16 h at 120° C., 2 h at 140° C. Purified on a chromatographic column (toluene:ethyl acetate 19:1→14:1). Yield: 2.44 g (92%). Brown fibrous crystals. M.p.: 167-169° C. $^1$H-NMR (500 MHz, CDCl$_3$): δ 8.65 (dd, J$_1$=1.1 Hz, J$_2$=3.9 Hz, 2H), 7.63 (dd, J$_1$=1.1 Hz, J$_2$=5.0 Hz, 2H), 7.23 (dd, J$_1$=3.9 Hz, J$_2$=5.0 Hz, 2H), 4.85 (t, J=5.7 Hz, 2H), 4.15 (d, J=5.7 Hz, 4H), 3.81-3.74 (m, 4H), 3.57-3.50 (m, 4H), 1.15 (t, J=7.0 Hz, 12H). $^{13}$C-NMR (125 MHz, CDCl$_3$): δ 161.9, 140.8, 134.5, 131.0, 129.7, 128.1, 107.8, 100.8, 64.0, 45.4, 15.3. HRMS (ESI) calc. for C$_{26}$H$_{32}$N$_2$O$_6$NaS$_2$(M+Na$^+$): 555.1594, found: 555.1599. Calc. elem. anal. (%) for the formula C$_{26}$H$_{32}$N$_2$O$_6$S$_2$: C, 58.62, H, 6.06, N, 5.26. found: C, 58.59; H, 6.06; N, 5.22.

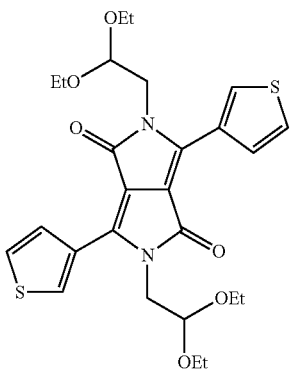 [SMILES: CCOC(CN1C(=O)C2=C(c3ccsc3)N(CC(OCC)OCC)C(=O)C2=C1c1ccsc1)OCC]

3.4 2,5-Di(2,2-diethoxyethyl)-1,4-diketo-3,6-di(3-thiophenyl)pyrrolo[3,4-c]pyrrole (2d)

Obtained from 1d (1.50 g, 5 mmol). Reaction time: 16 h. Purified on a chromatographic column (hexane:ethyl acetate 4:1). Yield: 1.40 g (52%). Reddish-orange solid. M.p.: 166-167° C. $^1$H-NMR (600 MHz, CDCl$_3$): δ 8.71 (dd, J$_1$=1.2 Hz, J$_2$=3.0 Hz, 2H), 8.11 (dd, J$_1$=1.2 Hz, J$_2$=5.1 Hz, 2H), 7.43 (dd, J$_1$=3.0 Hz, J$_2$=5.1 Hz, 2H), 4.91 (t, J=5.6 Hz, 2H), 3.97 (d, J=5.6 Hz, 4H), 3.84-3.78 (m, 4H), 3.61-3.55 (m, 4H), 1.19 (t, J=7.1 Hz, 12H). $^{13}$C-NMR (150 MHz, CDCl$_3$): δ 162.7, 142.8, 131.1, 129.2, 129.0, 126.0, 107.9, 101.3, 64.5, 45.9, 15.3. HRMS (ESI) calc. for C$_{26}$H$_{32}$N$_2$O$_6$NaS$_2$ (M+Na$^+$): 555.1594, found: 555.1596. Calc. elem. anal. (%) for the formula C$_{26}$H$_{32}$N$_2$O$_6$S$_2$: C, 58.62; H, 6.06; N, 5.26. found: C, 58.71, H, 5.98, N, 5.24.

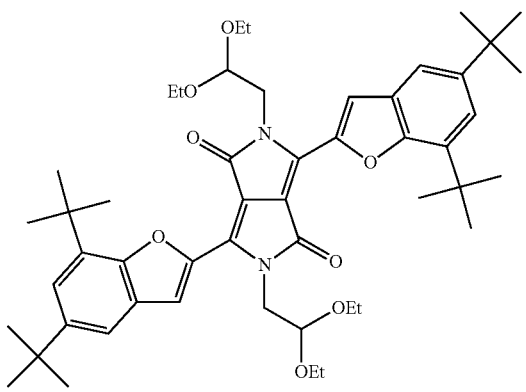 [SMILES: CCOC(CN1C(=O)C2=C(c3cc4cc(C(C)(C)C)cc(C(C)(C)C)c4o3)N(CC(OCC)OCC)C(=O)C2=C1c1cc2cc(C(C)(C)C)cc(C(C)(C)C)c2o1)OCC]

3.5 2,5-Di(2,2-diethoxyethyl)-1,4-diketo-3,6-di(5,7-di-t-butyl-2-benzofuryl)pyrrolo[3,4-c]pyrrole (2e)

Obtained from 1e (2.96 g, 5 mmol). Reaction time: 16 h. Purified on a chromatographic column (hexane:chloride methylene 1:3→pure methylene chloride). Yield: 2.71 g (66%). Brown fibrous crystals. M.p.: 194-196° C. $^1$H-NMR (500 MHz, CDCl$_3$): δ 8.77 (s, 2H), 7.56 (d, J=1.9 Hz, 2H), 7.41 (d, J=1.9 Hz, 2H), 4.77 (t, J=5.7 Hz, 2H), 4.55 (d, J=5.7 Hz, 4H), 3.74-3.67 (m, 4H), 3.46-3.39 (m, 4H), 1.57 (s, 18H), 1.39 (s, 18H), 1.07 (t, J=7.0 Hz, 12H). $^{13}$C-NMR (125 MHz, CDCl$_3$): δ 161.0, 152.4, 147.0, 144.9, 134.6, 134.4, 128.4, 122.7 117.1, 116.5, 108.5, 100.8, 62.9, 44.6, 34.9, 34.4, 31.7, 30.0, 15.2. HRMS (ESI) calc. for C$_{50}$H$_{68}$N$_2$O$_8$Na (M+Na$^+$): 847.4868, found: 847.4856. Calc. elem. anal. (%) for the formula C$_{50}$H$_{68}$N$_2$O$_8$: C, 72.78; H, 8.31; N, 3.40. found: C, 72.54; H, 8.12; N, 3.27.

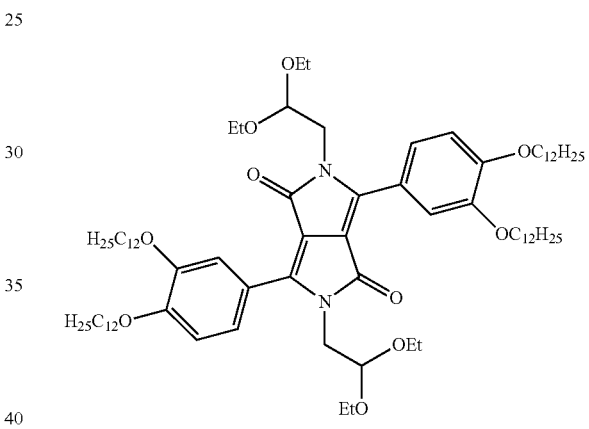

3.6 2,5-Di(2,2-diethoxyethyl)-1,4-diketo-3,6-di(3,4-didodecyloxyphenyl)pyrrolo[3,4-c]pyrrole (2f)

Obtained from 1f, yield 54%.

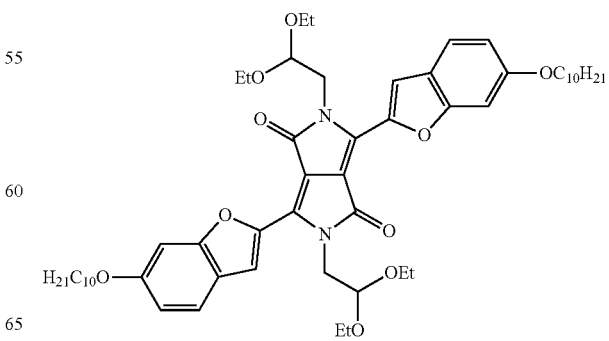

3.7 2,5-Di(2,2-diethoxyethyl)-1,4-diketo-3,6-di(6-decyloxy-2-benzofuryl)pyrrolo[3,4-c]pyrrole (2g)

Obtained from 1 g, yield 81%.

4. Cyclization of Acetals (Procedure A)

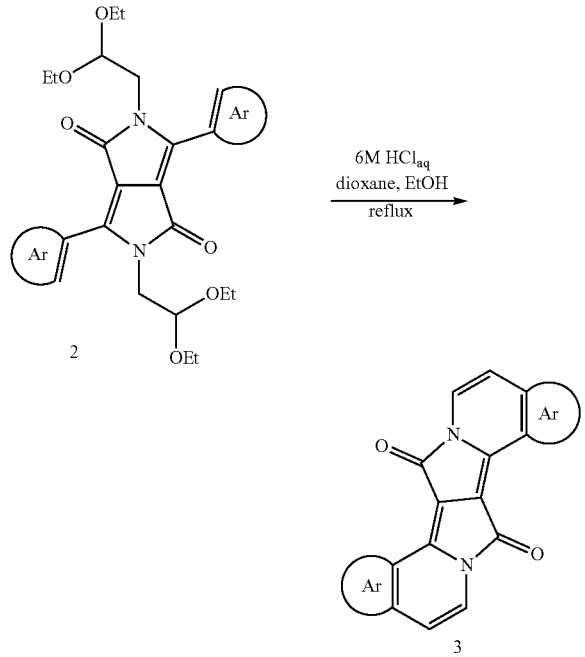

General Specification

Diacetal 2 (0.5 mmol) is dissolved in a hot mixture consisting of 2 ml ethanol and 9 ml dioxane and heated to boiling. Then 2 ml of 6M hydrochloric acid is added in one portion. After observing complete conversion of the substrate in TLC, the reaction mixture is cooled and diluted with 20 ml water. The precipitated product is filtered off and transferred to a beaker containing hot methanol. The hot suspension obtained is treated with ultrasound for tens of seconds, the precipitate is filtered off hot, washed with methanol and dried under reduced pressure.

4.1

(3a): Obtained from 2a (320 mg, 0.5 mmol). Reaction time: 1 h. Yield: 159 mg (70%). Dark violet powder. M.p.: >400° C. (decomposition). $^1$H-NMR (500 MHz, TFA-d): δ 8.65 (d, J=6.8 Hz, 2H), 8.47 (s, 2H), 8.27 (d, J=6.8 Hz, 2H), 7.73 (s, 2H), 4.40 (s, 6H), 4.35 (s, 6H). $^{13}$C-NMR (125 MHz, TFA-d): δ 168.5, 165.6, 157.3, 150.8, 144.5, 126.6, 125.6, 123.8, 109.5, 108.9, 59.3, 58.6. HRMS (EI 70 eV) calc. for $C_{26}H_{20}N_2O_6$ (M$^+$): 456.1321, found: 456.1324.

4.2

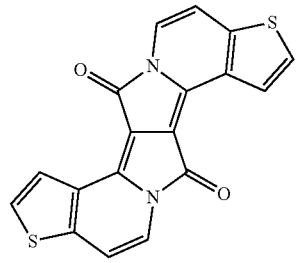

(3d): Obtained from 2d (266 mg, 0.5 mmol). Reaction time: 1 h. Yield: 110 mg (63%). Dark violet solid. M.p.: >400° C. $^1$H-NMR (500 MHz, DMSO-d$_6$, 80° C.): δ 8.01 (d, J=5.4 Hz, 2H), 7.97 (m, 4H), 7.39 (d, J=7.2 Hz, 2H). $^{13}$C-NMR (125 MHz, TFA-d): δ 167.7, 165.3, 147.7, 141.0, 136.7, 127.5, 127.2, 126.2, 124.3. HRMS (EI 70 eV) calc. for $C_{18}H_8N_2O_2S_2$ (M$^+$): 348.0027, found: 348.0031.

4.3

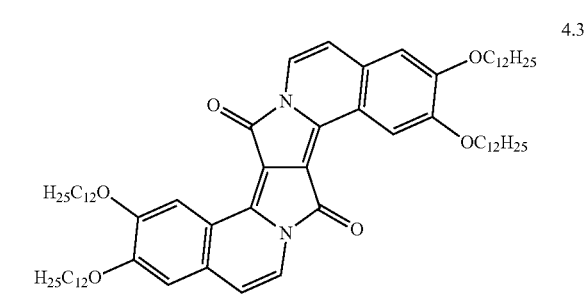

(3f): Yield 139 mg (71%). Dark violet crystals.

5. Cyclization of Acetals (Procedure B)

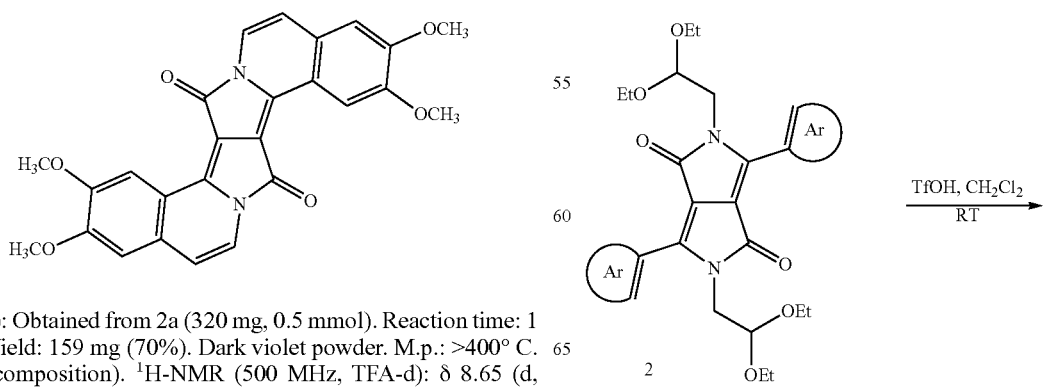

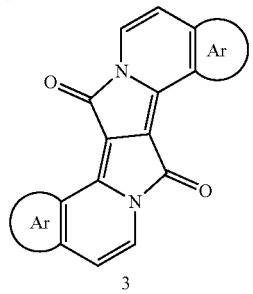

3

General Specification:

Diacetal 2 (0.5 mmol) is dissolved in 10 ml of methylene chloride. Then trifluoromethanesulphonic acid (0.97 ml, 11 mmol) is added slowly, and reaction is carried out at room temperature until the substrate has disappeared completely. Then the reaction mixture is transferred to a beaker containing 100 ml methanol, the precipitate is filtered off and diluted in boiling methanol. The hot suspension obtained is treated with ultrasound for tens of seconds, the product is filtered off hot, washed with hot methanol and dried under reduced pressure.

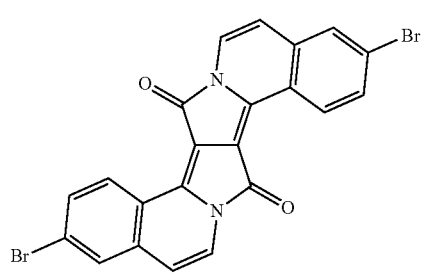

5.1

(3b): Obtained from 2b (339 mg, 0.5 mmol). Reaction time: 16 h. Yield: 197 mg (80%). Black powder. M.p.: >400° C. HRMS (EI 70 eV) calc. for $C_{22}H_{10}N_2O_2Br_2$ (M$^+$): 491.9109, found: 491.9117.

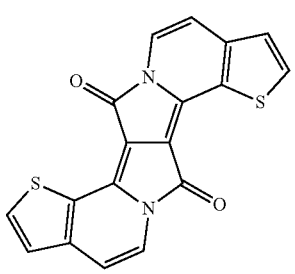

5.2

(3c): Obtained from 2c (266 mg, 0.5 mmol). Reaction time: 1 h. Yield: 130 mg (75%). Dark violet powder. M.p.: >400° C. (decomposition). $^1$H-NMR (600 MHz, DMSO-d$_6$, 80° C.): δ 8.20 (d, J=4.9 Hz, 2H), 7.96 (d, J=7.3 Hz, 2H), 7.52 (d, J=4.9 Hz, 2H), 7.19 (d, J=7.3 Hz, 2H). $^{13}$C-NMR (125 MHz, TFA-d): δ 167.3, 158.1, 156.1, 149.2, 137.7, 129.3, 128.3, 124.0. HRMS (EI 70 eV) calc. for $C_{18}H_8N_2O_2S_2$ (M$^+$): 348.0027, found: 348.0023.

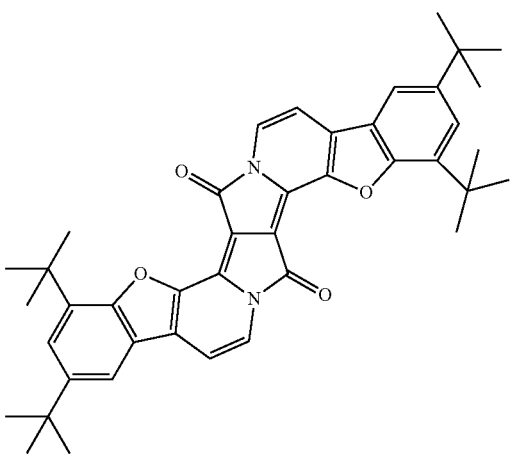

5.3

(3e): Obtained from 2e (413 mg, 0.5 mmol). Reaction time: 1 h. Yield: 287 mg (90%). Dark violet powder. M.p.: >400° C. $^1$H-NMR (200 MHz, CDCl$_3$): δ 8.16 (d, J=7.0 Hz, 2H), 7.72 (d, J=1.8 Hz, 2H), 7.59 (d, J=1.8 Hz, 2H), 7.19 (d, J=7.0 Hz, 2H), 1.68 (s, 18H), 1.44 (s, 18H). $^{13}$C-NMR (151 MHz, CDCl$_3$): δ 154.9, 154.4, 147.5, 145.6, 135.8, 129.3, 128.4, 124.7, 123.7, 122.6, 115.1, 105.5, 95.9, 35.1, 34.8, 31.7, 29.9. HRMS (EI 70 eV) calc. for $C_{42}H_{44}N_2O_4$ (M$^+$): 640.3301, found: 640.3294.

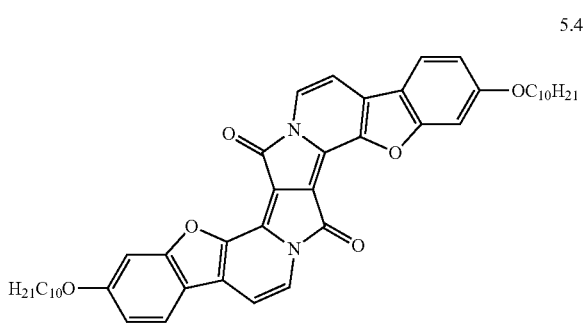

5.4

(3g): Yield: 250 mg (80%). Dark violet powder.

Application Example 1

Advantageous Properties of the Compounds According to the Invention

All the dyes obtained according to the invention display very strong absorption of visible light in the orange and red radiation range. This means that their colour fluctuates between deep violet and navy blue. These compounds emit red light (fluorescence). The precise optical parameters (i.e. absorption peak, emission peak, molar absorption coefficient and fluorescence quantum yield) are given in Table 1. All the most characteristic examples are included with the exception of compound 3b, which is a pigment and its solubility in all organic solvents (and water) is too low for it to be possible to measure the absorption and fluorescence spectrum. It is a crystalline solid of a violet-black colour.

TABLE 1

Optical parameters of the compounds of structure 3.

| Compound | $\lambda_{abs}$ [nm] | $\lambda_{em}$ [nm] | Stokesshift [cm$^{-1}$] | Molar absorption coefficient $\epsilon_{max}$ [M$^{-1}$ cm$^{-1}$] | Fluorescence quantum yield $\phi_{fl}{}^b$ |
|---|---|---|---|---|---|
| 3a | 593 | 600 | 200 | 110000 | 0.19 |
| 3c | 604 | 613 | 240 | 64000 | 0.13 |
| 3d | 574 | 582 | 240 | 73000 | 0.40 |
| 3e | 643 | 652 | 210 | 120000 | 0.04 |

Application Example 2

Bottom Gate Bottom Contact (BGBC) Field-Effect Transistors (FETs)

Heavily doped silicon wafers (Si n$^{--}$ (425±40 μm) with a 230 nm thick thermally grown silicon dioxide layer having on top of the silicon dioxide layer indium tin oxide (15 nm)/gold (30 nm) contacts are used as substrates. The substrates are prepared by cleaning in acetone and i-propanol followed by oxygen plasma treatment for 30 minutes and are then transferred in a glove box and treated with octyltrichlorosilane (OTS) to achieve a hydrophobic monolayer.

The semiconductor 3e is dissolved in o-dichlorobenzole (o-DCB) in a concentration of 0.75% by weight at elevated temperature and drop-casted onto the silicon dioxide/silicon substrate.

All electrical measurements are performed under a nitrogen atmosphere in a glove box with a gate voltage (Vg) varying from 10 to −30 V and at a drain voltage (Vd) equal to 3 and 30V for the transfer characterisation. For the output characterization Vd is varied from 0 to −30V at Vg=0, 10, 20, 30 V. The reported mobilities represent the saturation mobilities at Vd=−30V.

The results of BGBC FET measurements are shown in Table 2 below.

| Appl. Example | Semiconductor | Solvent | Sat. Mobility, cm$^2$/VS | On/Off | Uth, V |
|---|---|---|---|---|---|
| 2 | 3e | o-DCB | 1.8 * 10$^{-4}$ | 1 * 10$^{+4}$ | −12.4 |

Application Example 2

Bottom Gate Top Contact (BGTC) Field-Effect Transistors (FETs)

Sample Preparation:
i) OTS Treatment:
a) The substrate is cleaned with an oxygen-plasma treatment for 2 minutes.
b) The substrate is immersed in an 0.2% vol solution of OTS in toluene for 20 minutes.
c) The substrate is transferred to an beaker containing only toluene, in order to remove excess OTS from it. Subsequently the substrate is blown dry with nitrogen.
d) The substrate is put into an oven set at 90° C. for 30 minutes.
e) Finally the substrate is sonicated in toluene for 5 minutes.

ii) Evaporation of Semiconductor:
30 nm thick layers of the semiconductors are thermally evaporated in high vacuum (pressure: 3*10$^{-6}$ mbar) at an evaporation rate of 0.2 A/sec.

iii) Evaporation of Gold Contacts:
50 nm thick gold contacts are thermally evaporated through a polyimide shadow mask in high vacuum.

iv) Electrical Characterization:
All measurements were performed with an Agilent 4145C Semiconductor Parameter Analyzer at room temperature in ambient air and ambient light.

Measurement Range:

| | |
|---|---|
| Transfer characteristics: | UGS: 20 V to −60 V in 2 V steps UDS: −40 V |
| Output characteristics: | UDS: 0 V to −60 V in 2 V steps. UGS: 0 V, −15 V, −30 V, −45 V, 60 V. |

The measurements are performed on transistors with a channel width W of 200 μm and a channel length L of 100 μm. The dielectric is silicon dioxide with a permittivity of $\square_r$=3.9 and a total thickness d of 100 or 300 nm.

The field-effect mobility μ is obtained from the slope of the square-root of the drain current m in the saturation regime (red curve in the transfer characteristics). The slope is extracted with the help of the dashed black line. The region for the extraction of the slope is selected with respect to a good correlation between the square root of the drain current (red line) and the dashed black line. (The borders of the region selected for the slope extraction are marked by the vertical dashed blue and red lines). The threshold voltage is extracted from the interception of the dashed black line and the x-axis.

The Results of BGTC FET measurements are shown in Table 3 below.

| Material | Temp. | Max mobility | Ion/off | Uth |
|---|---|---|---|---|
| 3e | 100° C. | 1.2 * 10$^{-3}$ cm$^2$/Vsec | 1.0E+04 | 2.44 V |
| 3d | 100° C. | 3 * 10$^{-5}$ cm$^2$/Vsec | 2.4E+02 | 1.36 V |

Application Example 3

Cyclic Voltammograms (CVs)

CVs of the films were recorded on a Autolab PGSTAT302 potentiostat in acetonitrile containing tetrabutylammonium-tetrafluoroborate (Bu$_4$NBF$_4$, 0.1M) as supporting electrolyte at scan rate 100 mV/s. Counter and working electrodes were made of Pt, and the reference electrode was Ag/AgCl. Films were drop casted on the Pt disc working electrode. All the potentials were calibrated vs. Ferrocene/Ferrocenium redox couple and HOMO/LUMO values were calculated as follows:

HOMO(CV)=−4.8-E$^{ox}_{onset}$
LUMO (CV)=−4.8-E$^{red}_{onset}$

The values measured for compounds are reported in Table 4.

| Compound | Onset UV, nm | BG, eV | HOMO (CV), eV | LUMO (CV), eV |
|---|---|---|---|---|
| 3d | 596 | 2.08 | −5.67 | — |
| 3c | 633 | 1.96 | −5.643 | −3.322 |
| 3e | 674 | 1.84 | −5.606 | −3.406 |

The invention claimed is:

1. A compound of formula (III):

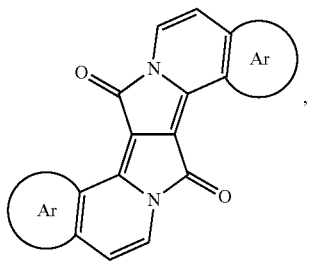

wherein Ar is a homo- or heteroaromatic system.

2. The compound according to claim 1,
wherein Ar is a homo- or heteroaromatic system, which is selected from

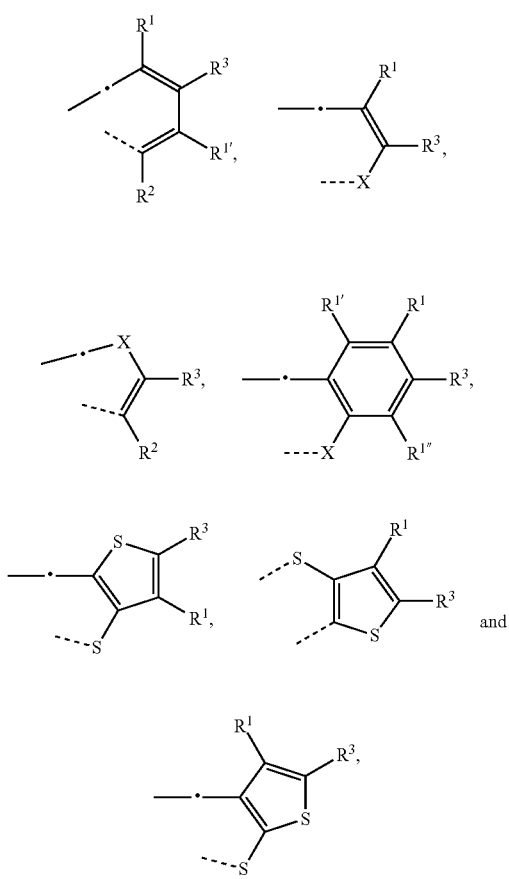

wherein the dotted lines are bonds to the 6-membered ring, the dotted line —·— is a bond to a carbon atom in para-position to the nitrogen atom, the dotted line ······ is a bond to a carbon atom in meta-position to the nitrogen atom, wherein R', R¹' and R¹'' are each independently H, F, cyano, $C_1$-$C_{25}$alkoxy, $C_1$-$C_{25}$alkyl substituted with a halogen atom, or $C_1$-$C_{25}$alkyl, $R^2$ is H, F, cyano, $C_1$-$C_{25}$alkoxy, or $C_1$-$C_{25}$alkyl, $R^3$ is hydrogen, F, cyano, $C_1$-$C_{25}$ alkoxy, $C_1$-$C_{25}$alkyl substituted with a halogen atom, $C_1$-$C_{25}$alkyl,

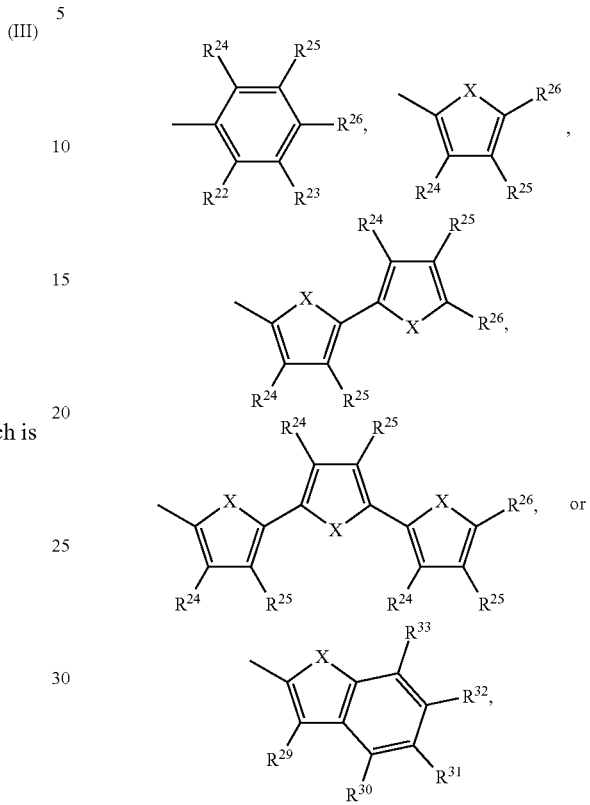

wherein $R^{22}$ to $R^{25}$ and $R^{29}$ to $R^{33}$ are each independently H, F, cyano, $C_1$-$C_{25}$alkoxy, $C_1$-$C_{25}$alkyl substituted with a halogen atom, or $C_1$-$C_{25}$alkyl, and $R^{26}$ is H, F, cyano, phenyl, $C_1$-$C_{25}$alkoxy, $C_1$-$C_{25}$alkyl substituted with a halogen atom, or $C_1$-$C_{28}$alkyl;

X is O, S, Se, or $NR^4$, $R^4$ is hydrogen, $C_6$-$C_{18}$aryl; $C_6$-$C_{18}$aryl which is substituted by $C_1$-$C_{18}$alkyl, or $C_1$-$C_{18}$alkoxy; $C_1$-$C_{25}$alkyl, which may optionally be interrupted by an oxygen or sulphur atom and/or is optionally substituted by a halogen atom; or $C_7$-$C_{25}$arylalkyl.

3. The compound according to claim 2, which is a compound of formula

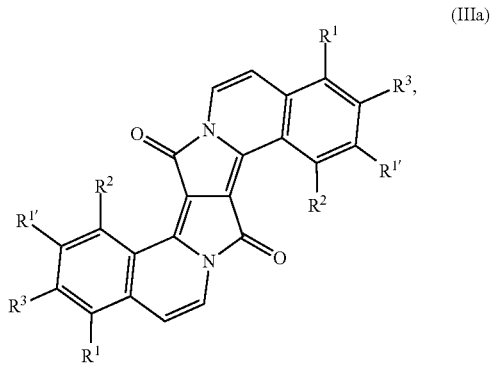

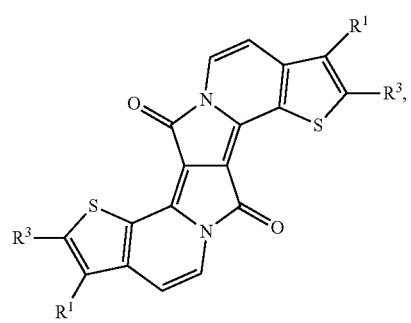 (IIIb)
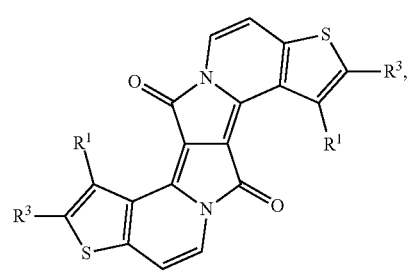 (IIIc)
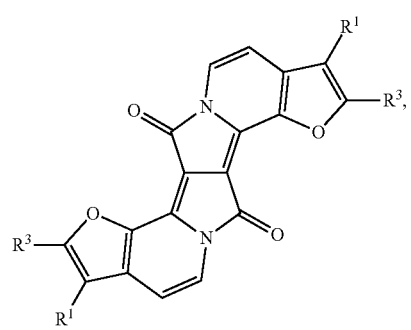 (IIId)
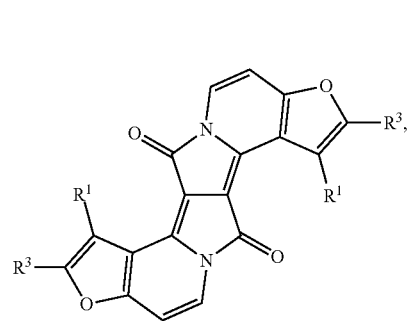 (IIIe)
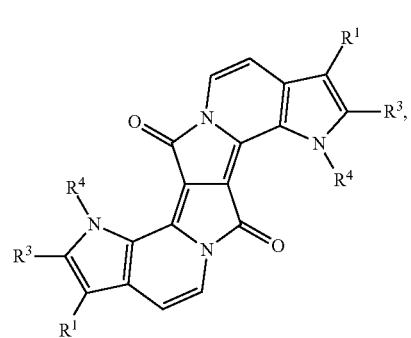 (IIIf)
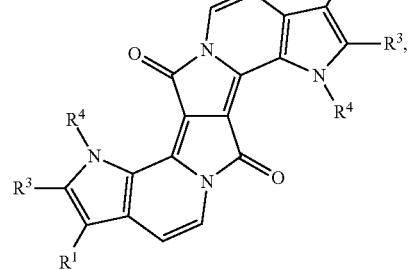 (IIIg)
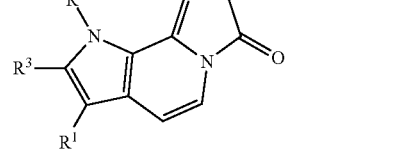 (IIIh)
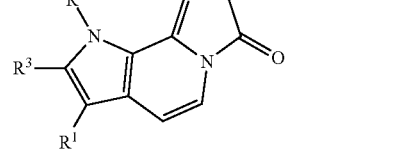 (IIIi)
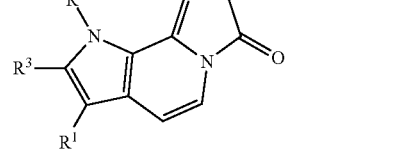 (IIIj)

(IIIk)
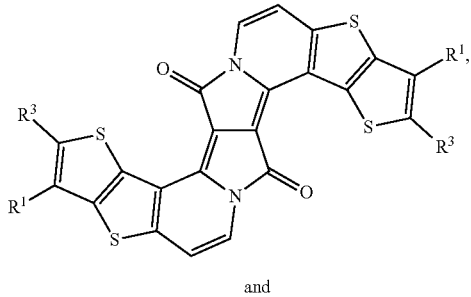
and
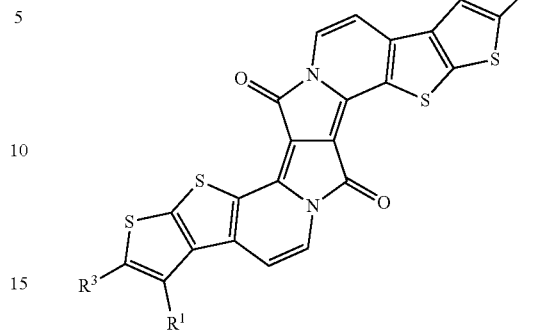
wherein
R¹, R¹', R¹'', R², R³ and R⁴ are as defined in claim 2.
4. The compound according to claim 1, wherein the compound is selected from the group consisting of the compounds of formulae 3a, 3b, 3c, 3d, 3e, 3f, 3g, 4a, 4b, and 4c:
(3a)
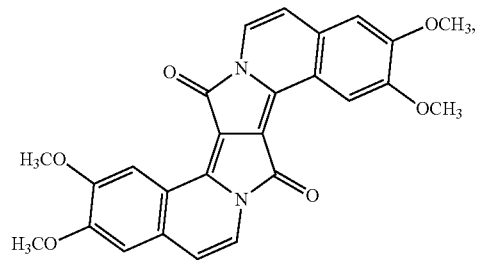
(3b)
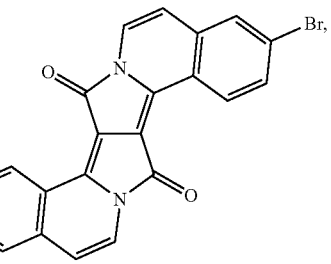
(3c)
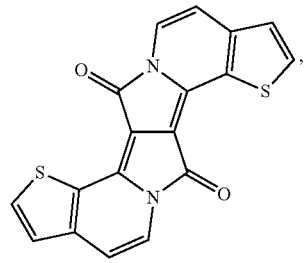
(3d)
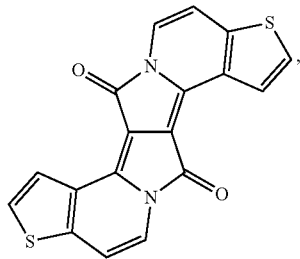
(3e)
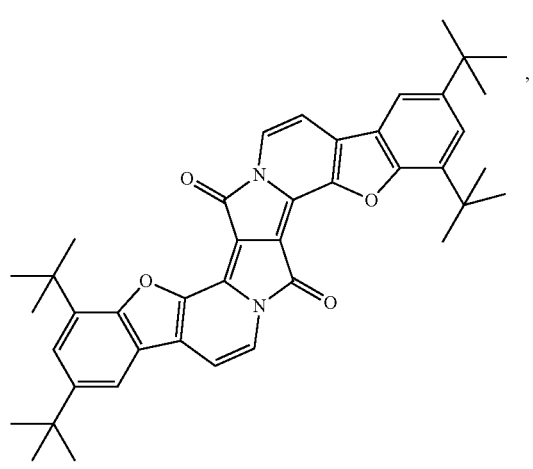
(3f)
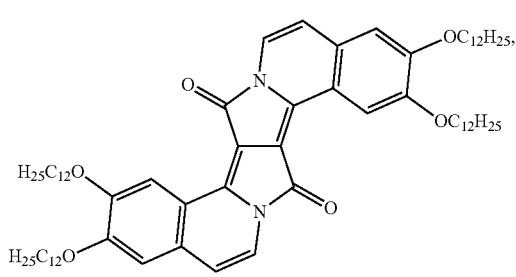

-continued
(3g)
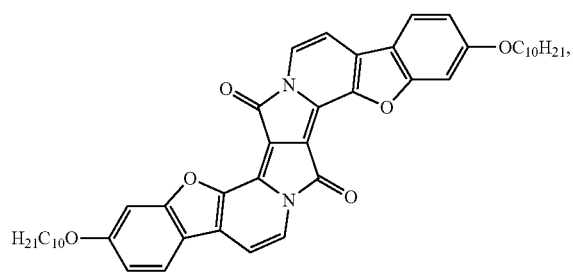
(4a)
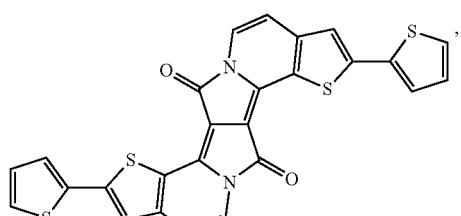
(4b)
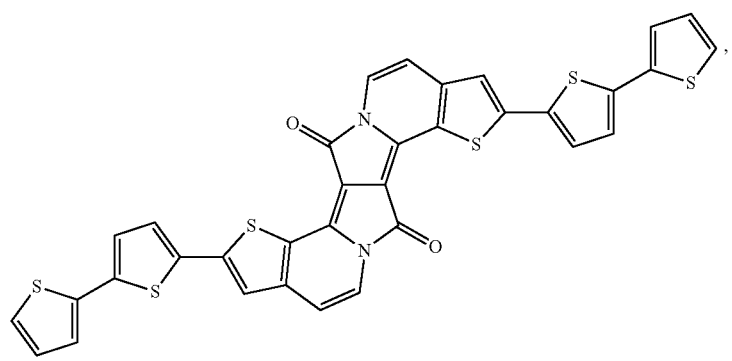
and
(4c)
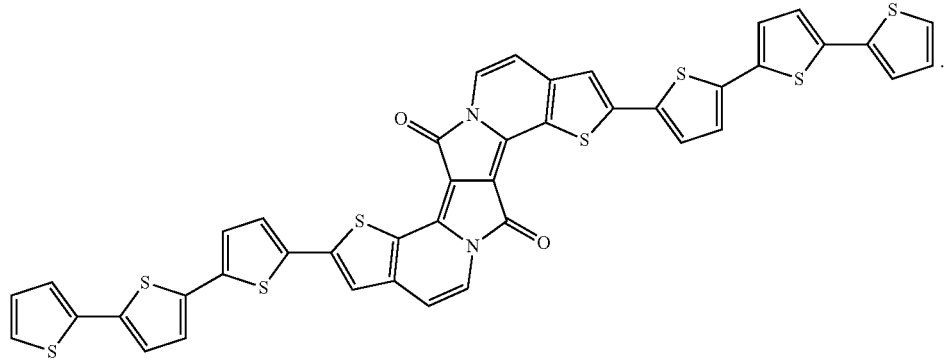
5. A method for the production of a compound of formula (III) according to claim 1:
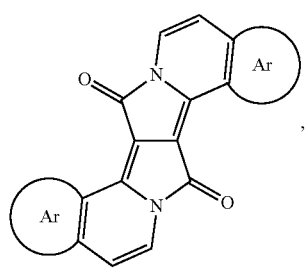
(III)
where Ar is a homo- or heteroaromatic system, the method comprising:
a) alkylating a diketopyrollopyrrole of formula (I):
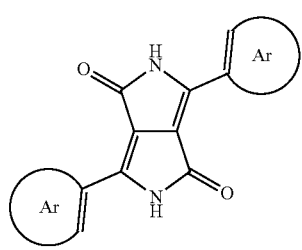
(I)

in a reaction with an acetal, and then b) subjecting the N-alkylated derivative of formula (II) obtained in the alkylating a)

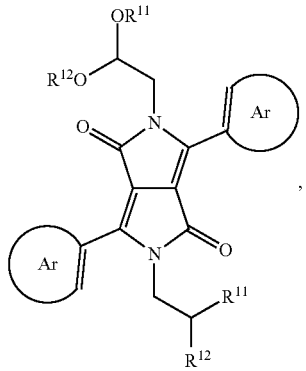
(II)

in the presence of an acid to intramolecular condensation, obtaining the compound of formula (III), wherein $R^{11}$ and $R^{12}$ are $C_1$-$C_8$alkyl, or together form a ring 6. The method according to claim 5, wherein a) the alkylation reaction is carried out in the presence of tetrabutylammonium hydrogen sulfate, $K_2CO_3$ and dimethylformamide (DMF), and the product obtained is isolated from the reaction mixture by extraction.

7. The method according to claim 5, wherein in the subjecting b) the cyclization reaction is carried out in a mixture of ethanol and dioxane in the presence of HCl.

8. The method according to claim 5, wherein in the subjecting b) the cyclization reaction is carried out in methylene chloride in the presence of trifluoromethanesulphonic acid.

9. An organic semiconductor material, layer or component, comprising a compound according to claim 1.

10. A semiconductor device, comprising a compound according to claim 1.

11. The semiconductor device according to claim 10, which is an organic photovoltaic device, a photodiode, or an organic field effect transistor.

12. A process for the preparation of an organic semiconductor device, comprising either:
applying a solution and/or dispersion of a compound according to claim 1 in an organic solvent to a substrate and removing the solvent; or
evaporating the compound according to claim 1.

13. A compound of formula

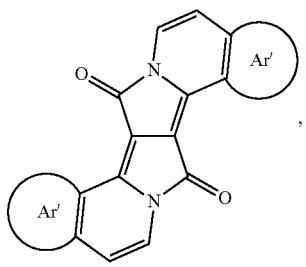
(V)

wherein Ar' is a homo- or heteroaromatic system, which is selected from

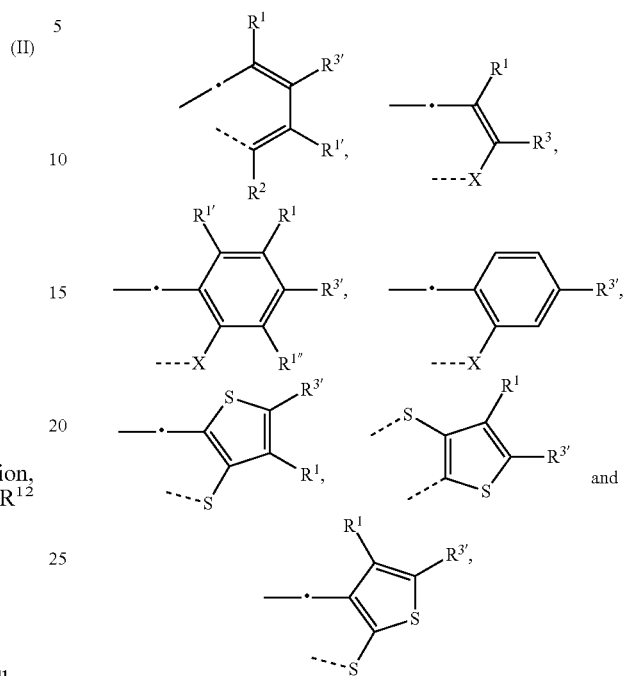

wherein the dotted lines are bonds to the 6-membered ring, the dotted line — - — is a bond to a carbon atom in para-position to the nitrogen atom, the dotted line - - - - - - is a bond to a carbon atom in meta-position to the nitrogen atom, wherein $R^1$, $R^{1'}$ and $R^{1''}$ are each independently H, halogen, cyano, $C_1$-$C_{25}$alkoxy, $C_1$-$C_{25}$alkyl substituted with a halogen atom, or $C_1$-$C_{25}$alkyl, $R^2$ is H, halogen, cyano, $C_1$-$C_{25}$alkoxy, or $C_1$-$C_{25}$alkyl, $R^{3'}$ is Cl, Br, or I,

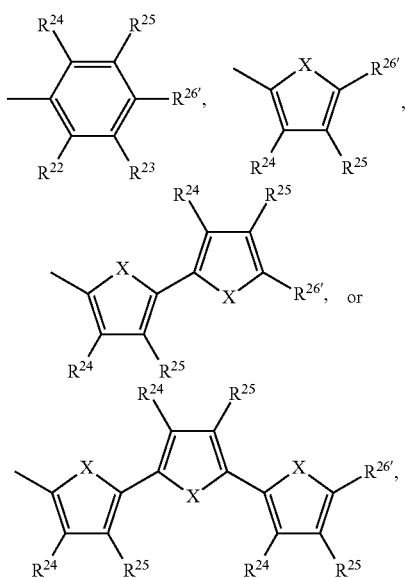

wherein $R^{22}$ to $R^{25}$ are each independently H, halogen, cyano, $C_1$-$C_{25}$alkoxy, $C_1$-$C_{25}$allyl substituted with a halogen atom, or $C_1$-$C_{25}$alkyl, and $R^{26'}$ is Cl, Br, or I;

X is O, S, Se, or $NR^4$, $R^4$ is hydrogen, $C_6$-$C_{18}$aryl; $C_6$-$C_{18}$aryl which is substituted by $C_1$-$C_{18}$alkyl, or $C_1$-$C_{18}$alkoxy; $C_1$-$C_{25}$alkyl, which may optionally be interrupted by an oxygen or sulphur atom and/or is optionally substituted by a halogen atom; or $C_7$-$C_{25}$arylalkyl.

14. The compound according to claim 13, which is a compound of formula

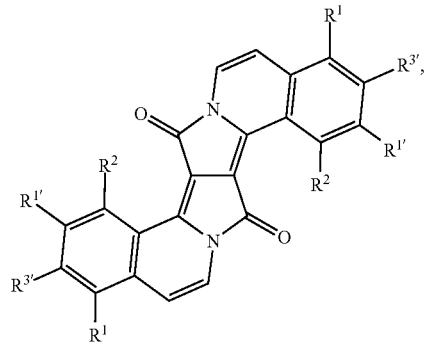
(Va)

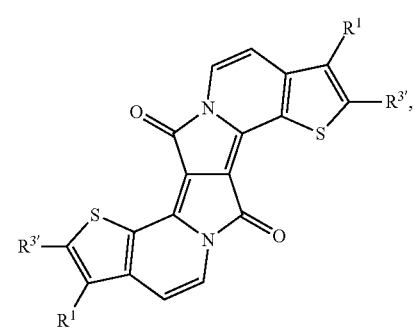
(Vb)

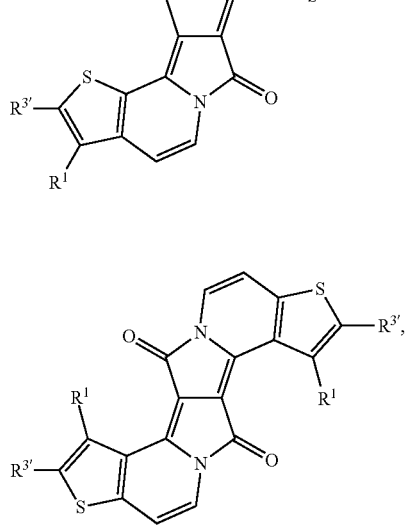
(Vc)

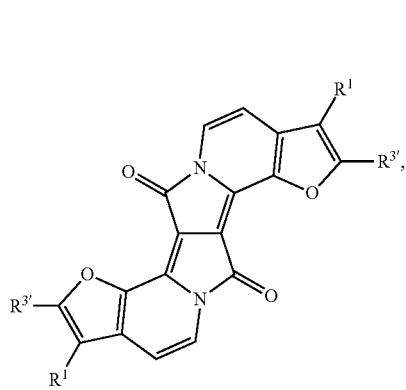
(Vd)

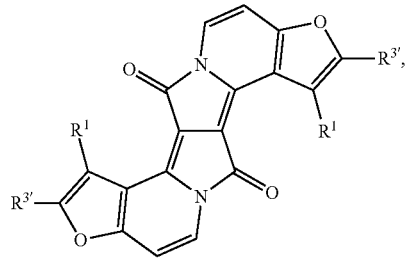
(Ve)

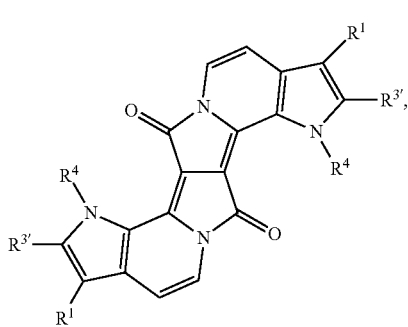
(Vf)

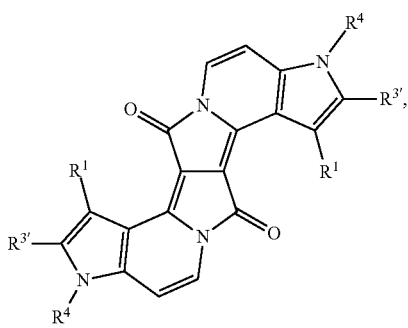
(Vg)

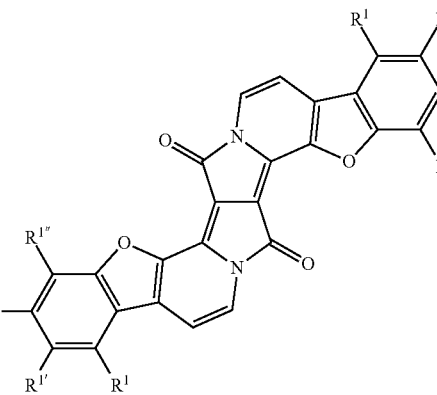
(Vh)

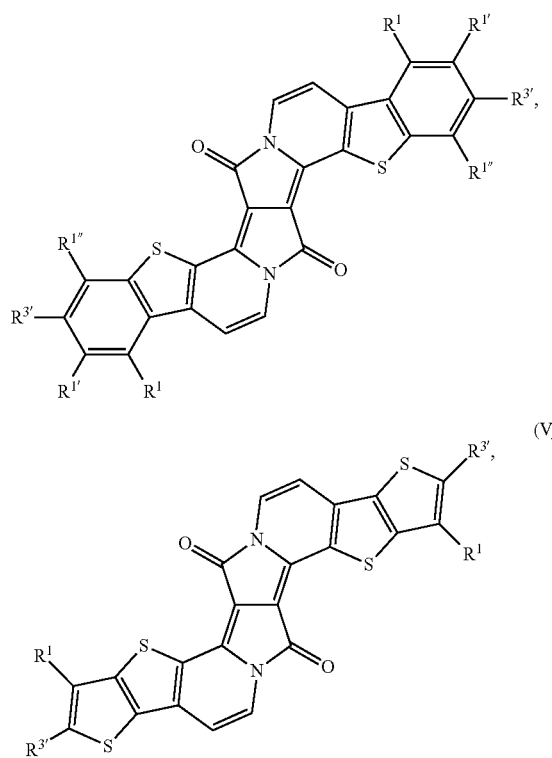
(Vi)
(Vj)
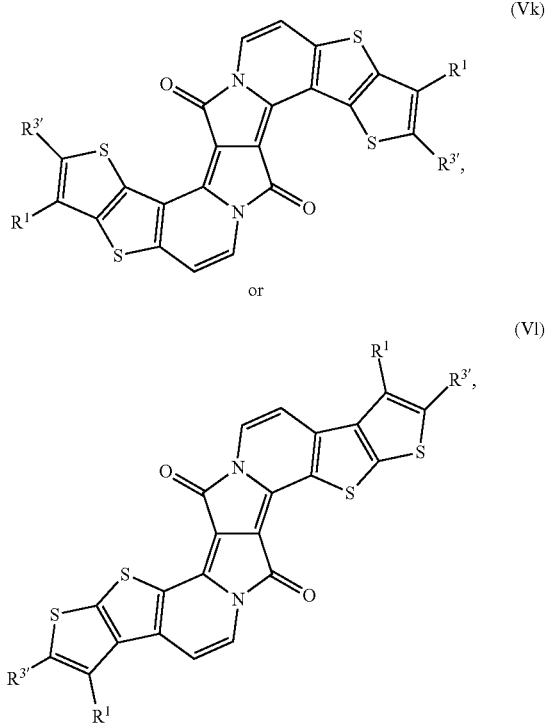
(Vk)
or
(Vl)
wherein $R^1$, $R^{1'}$, $R^{1''}$, $R^2$, $R^{3'}$ and $R^4$ are as defined in claim 13.
15. The compound according to claim 13, wherein the compound is selected from
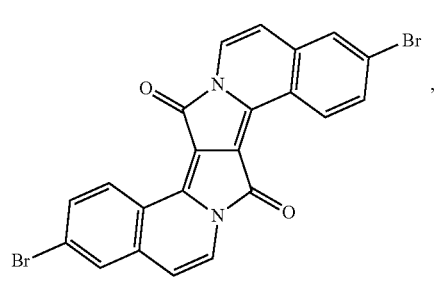
(3b)
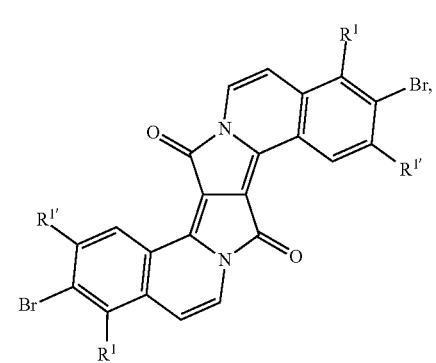
(5a)
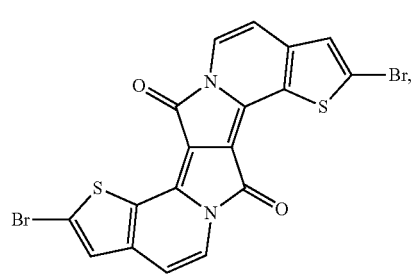
(5b)
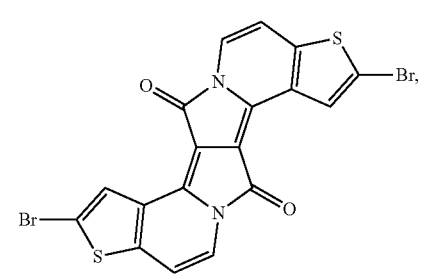
(5c)

-continued
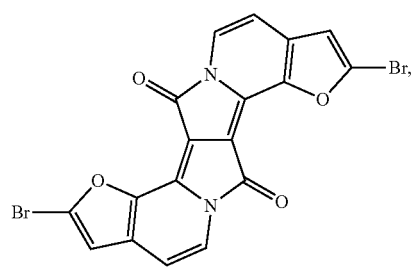 (5d)
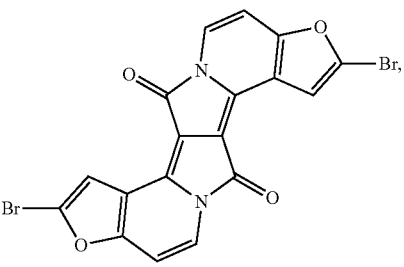 (5e)
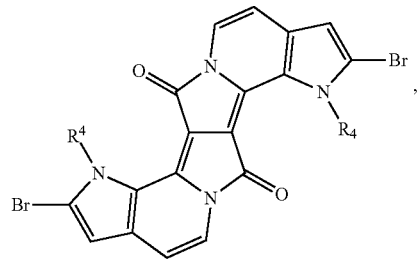 (5f)
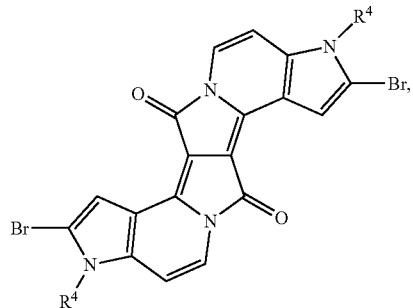 (5g)
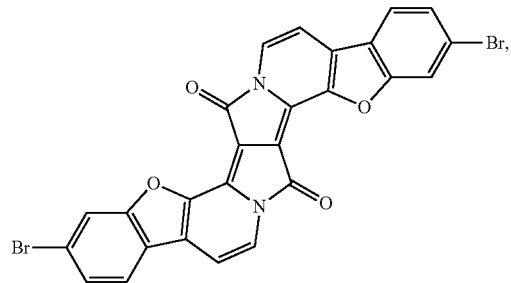 (5h)
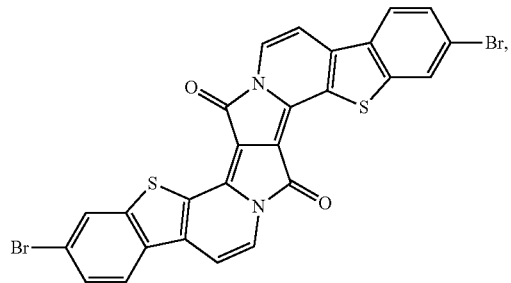 (5i)
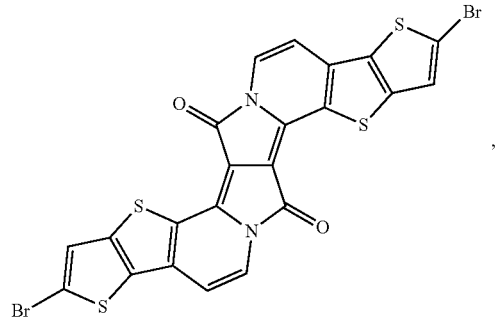 (5j)
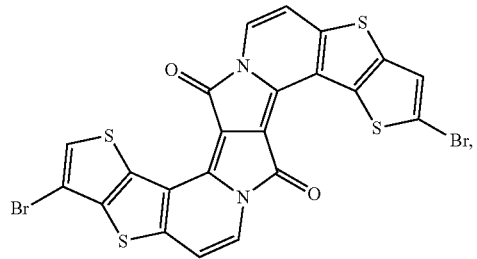 (5k)
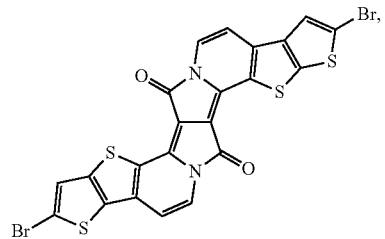 (5l)
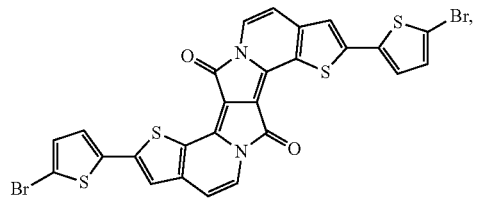 (5m)
and -continued
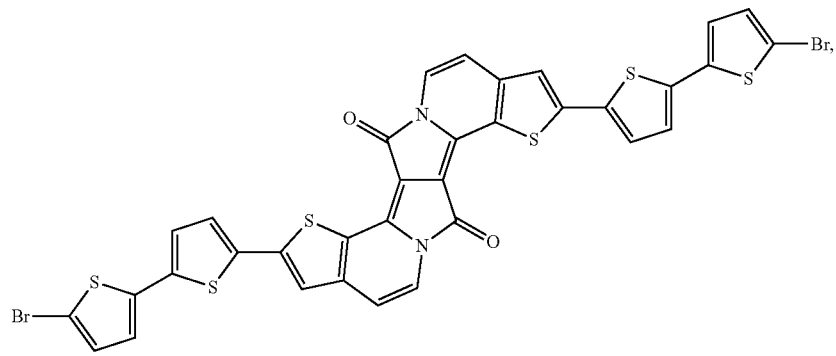
(5n)
wherein R¹ and R¹ are each independently hydrogen or C₁-C₂₅alkyl.
16. The compound according to claim 2, wherein $R^1$, $R^{1'}$, and $R1''$ are each independently H, C₁-C₂₅alkoxy, or C₁-C₂₅alkyl.
17. The compound according to claim 2, wherein $R^2$ is H, C₁-C₂₅alkoxy, or C₁-C₂₅alkyl.
18. The compound according to claim 2, wherein $R^3$ is hydrogen, F, cyano, C₁-C₂₅alkyl,
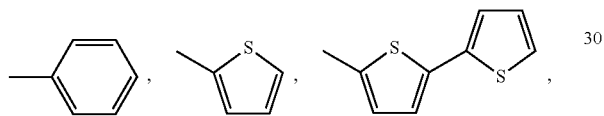
-continued
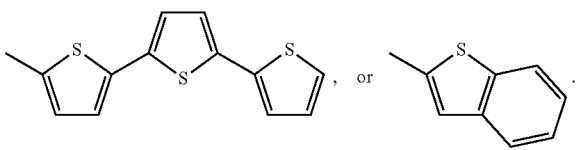
* * * * *